United States Patent
Shim et al.

(10) Patent No.: US 10,386,224 B2
(45) Date of Patent: Aug. 20, 2019

(54) FLEXIBLE CONDUCTIVE APPARATUS AND SYSTEMS FOR DETECTING PRESSURE

(71) Applicant: STUDIO 1 LABS INC., Toronto (CA)

(72) Inventors: Edward Sup Shim, Toronto (CA); Ying-Hsin Lin, Toronto (CA)

(73) Assignee: STUDIO 1 LABS INC., Toronto (CA)

( * ) Notice: Subject to any disclaimer, the term of this patent is extended or adjusted under 35 U.S.C. 154(b) by 0 days.

(21) Appl. No.: 16/099,964

(22) PCT Filed: Oct. 24, 2017

(86) PCT No.: PCT/CA2017/051267
§ 371 (c)(1),
(2) Date: Nov. 8, 2018

(87) PCT Pub. No.: WO2018/076106
PCT Pub. Date: May 3, 2018

(65) Prior Publication Data
US 2019/0145817 A1    May 16, 2019

Related U.S. Application Data

(60) Provisional application No. 62/412,438, filed on Oct. 25, 2016.

(51) Int. Cl.
*G01L 1/22* (2006.01)
*G01H 11/06* (2006.01)
(Continued)

(52) U.S. Cl.
CPC ............ *G01H 11/06* (2013.01); *A61B 5/024* (2013.01); *A61B 5/08* (2013.01); *A61B 17/132* (2013.01);
(Continued)

(58) Field of Classification Search
CPC ... G01L 19/147; G01L 9/0042; G01L 9/0072; G01L 13/025; G01L 19/04; G01L 9/0054;
(Continued)

(56) References Cited

U.S. PATENT DOCUMENTS

| 4,033,332 A | 7/1977 | Hardway et al. |
| 4,644,101 A | 2/1987 | Jin et al. |

(Continued)

FOREIGN PATENT DOCUMENTS

| CA | 2225945 A1 * | 7/1998 | ............. B60N 2/002 |
| CN | 102414546 A | 4/2012 | |

(Continued)

OTHER PUBLICATIONS

Juan Miguel Andujar Morgado, Andreas Konig; Low-Power Concept and Prototype of Distributed Resistive Pressure Sensor Array for Smart Floor and Surfaces in Intelligent Environments; 2012—9th International Multi-Conference on Systems, Signals and Devices.

(Continued)

*Primary Examiner* — Andre J Allen
(74) *Attorney, Agent, or Firm* — Ridout & Maybee LLP

(57) ABSTRACT

A variable conductive apparatus responsive to an applied external force for use in a variable pressure sensor, monitoring system, or other devices. The variable conductive apparatus comprises a first conductive path that includes a first conductive surface; a second conductive path that includes a second conductive surface, a part of the second conductive surface having a conductive contact surface area with a part of the first conductive surface when there is no applied external force, another part of the second conductive surface separate from another part of the first conductive surface when there is no applied external force, wherein the applied external force increases conductive contact surface area between the first conductive surface and the second (Continued)

US 10,386,224 B2

Page 2 conductive surface and results in an increase in conductivity between the first conductive surface and the second conductive surface.

32 Claims, 26 Drawing Sheets

(51) Int. Cl.

| | |
|---|---|
| *G01N 3/08* | (2006.01) |
| *G01L 1/14* | (2006.01) |
| *G01L 1/20* | (2006.01) |
| *B25J 19/02* | (2006.01) |
| *B25J 13/08* | (2006.01) |
| *A61B 17/132* | (2006.01) |
| *A61B 34/00* | (2016.01) |
| *A61B 34/30* | (2016.01) |
| *A61B 5/024* | (2006.01) |
| *A61B 5/08* | (2006.01) |
| *A61B 5/11* | (2006.01) |
| *A61B 5/113* | (2006.01) |
| *A61B 17/00* | (2006.01) |
| *A61B 90/00* | (2016.01) |

(52) U.S. Cl.
CPC .......... *A61B 17/1322* (2013.01); *A61B 34/30* (2016.02); *A61B 34/76* (2016.02); *B25J 13/084* (2013.01); *B25J 19/028* (2013.01); *G01L 1/146* (2013.01); *G01L 1/205* (2013.01); *G01L 1/2287* (2013.01); *G01N 3/08* (2013.01); *A61B 5/02444* (2013.01); *A61B 5/1102* (2013.01); *A61B 5/113* (2013.01); *A61B 5/1113* (2013.01); *A61B 5/1117* (2013.01); *A61B 2017/00022* (2013.01); *A61B 2017/00088* (2013.01); *A61B 2017/00119* (2013.01); *A61B 2034/741* (2016.02); *A61B 2090/064* (2016.02); *A61B 2090/065* (2016.02); *A61B 2562/0247* (2013.01)

(58) Field of Classification Search
CPC ............... G01L 9/0075; G01L 19/0038; G01L 19/0084; G01L 19/14; G01L 19/0069; G01L 19/0618; G01L 9/0055; G01L 9/0073; G01L 19/0092; G01L 19/0645; G01L 19/143; G01L 9/0051; G01L 9/0052; G01L 11/025; G01L 19/0007; G01L 19/0046; G01L 19/06; G01L 19/0627; G01L 19/0681; G01L 9/00; G01L 9/0041; G01L 9/0044; G01L 11/04; G01L 19/0023; G01L 19/069; G01L 19/142; G01L 19/16; G01L 27/002; G01L 7/00; G01L 7/163; G01L 7/166; G01L 9/0047; G01L 11/02; G01L 13/00; G01L 15/00; G01L 19/003; G01L 19/0609; G01L 19/0672; G01L 19/083; G01L 19/10; G01L 19/148; G01L 7/08; G01L 7/082; G01L 9/0045; G01L 9/0048; G01L 9/006; G01L 9/007; G01L 9/0076; G01L 9/045; G01L 9/06; G01L 9/065; G01L 9/12; G01L 9/125; G01L 11/00; G01L 17/00; G01L 19/00; G01L 19/0015; G01L 19/0076; G01L 19/02; G01L 19/08; G01L 19/141; G01L 19/145; G01L 19/146; G01L 1/142; G01L 1/2262; G01L 1/246; G01L 21/12; G01L 23/16; G01L 27/005; G01L 27/007; G01L 7/04; G01L 7/063; G01L 7/084; G01L 7/086; G01L 7/16; G01L 9/0002; G01L 9/0007; G01L 9/0016; G01L 9/0019; G01L 9/0022; G01L 9/0027; G01L 9/0033; G01L 9/0039; G01L 9/005; G01L 9/0058; G01L 9/0077; G01L 9/0079; G01L 9/008; G01L 9/0092; G01L 9/0095; G01L 9/025; G01L 9/04; G01L 9/08; G01L 9/085; G01L 9/105; G01L 9/14; G01L 9/16
USPC ........................................................ 73/159
See application file for complete search history.

(56) References Cited

U.S. PATENT DOCUMENTS

| | | | |
|---|---|---|---|
| 4,795,998 A * | 1/1989 | Dunbar ................. | G01L 1/205 |
| | | | 338/208 |
| 5,033,291 A | 7/1991 | Podoloff et al. | |
| 5,295,490 A | 3/1994 | Dodakian | |
| 5,878,620 A | 3/1999 | Gilbert et al. | |
| 6,210,771 B1 | 4/2001 | Post et al. | |
| 6,280,392 B1 | 8/2001 | Yoshimi et al. | |
| 6,461,307 B1 | 10/2002 | Krisbjarnarson et al. | |
| 6,826,968 B2 | 12/2004 | Manaresi et al. | |
| 6,932,774 B2 | 8/2005 | Nakatani et al. | |
| 7,201,063 B2 | 4/2007 | Taylor | |
| 7,395,717 B2 | 7/2008 | DeAngelis et al. | |
| 8,161,826 B1 | 4/2012 | Taylor | |
| 8,766,925 B2 | 1/2014 | Perlin et al. | |
| 8,800,386 B2 | 8/2014 | Taylor | |
| 9,032,804 B2 * | 5/2015 | Granado ................ | G01L 9/0052 |
| | | | 73/700 |
| 9,072,437 B2 | 7/2015 | Paalasmaa | |
| 2005/0096559 A1 | 5/2005 | Yanai | |
| 2008/0183095 A1 | 7/2008 | Austin et al. | |
| 2009/0099480 A1 | 4/2009 | Salgo et al. | |
| 2009/0282671 A1 | 11/2009 | Tao et al. | |
| 2014/0090488 A1 * | 4/2014 | Taylor ................... | G01L 1/18 |
| | | | 73/862.625 |
| 2015/0173671 A1 | 6/2015 | Paalasmaa et al. | |
| 2015/0351556 A1 | 12/2015 | Franceschetti | |
| 2016/0048235 A1 | 2/2016 | Poupyrev | |
| 2016/0157780 A1 | 6/2016 | Rimminen et al. | |
| 2016/0223416 A1 * | 8/2016 | Tao ......................... | G01L 1/20 |
| 2017/0028165 A1 | 2/2017 | Franceschetti | |
| 2017/0231089 A1 * | 8/2017 | Van Keymeulen .... | H05K 1/038 |
| 2018/0113032 A1 * | 4/2018 | Dickey .................. | G01L 1/142 |
| 2019/0024267 A1 * | 1/2019 | Hung .................... | D03D 1/0088 |
| 2019/0137322 A1 * | 5/2019 | Choi ....................... | G01G 3/13 |

FOREIGN PATENT DOCUMENTS

| | | | | |
|---|---|---|---|---|
| GB | 2341933 A | 3/2000 | | |
| WO | 2013109892 | 7/2013 | | |
| WO | WO-2014204323 A1 * | 12/2014 | ......... | A41D 13/1281 |
| WO | 2016025554 | 2/2016 | | |
| WO | 2016053731 | 4/2016 | | |
| WO | 2016124817 | 8/2016 | | |
| WO | 2016182860 | 11/2016 | | |

OTHER PUBLICATIONS

E. Ghafar-Zadeh, Dept. Of EECS, York University; 3rd Report NSERC ENGAGE, Wireless Continuous Respiratory Monitoring Using Conductive Fabrics, Apr. 12, 2017.
E. Ghafar-Zadeh, Dept. Of EECS, York University; 5th Report NSERC ENGAGE, Wireless Continuous Respiratory Monitoring Using Conductive Fabrics.
Ozgur Turel and Konstantin Likharev; CrossNets: possible neuromorphic networks based on nanoscale components; International Journal of Circuit Theory and Applications; Int. J. Circ. Theor. Appl. 2003; 31:37-52 (DOI: 10/1002/cta.223); Copyright 2003 John Wiley & Sons, Ltd.
International Search Report and Written Opinion dated Jan. 18, 2018 for PCT/CA2017/051267.

(56) References Cited

OTHER PUBLICATIONS

Giovanelli, D., Farella E., Force sensing resistor and evaluation of technology for wearable body pressure sensing, Journal of Sensors. 2016, Feb. 21, 2016.
Stoppa M., Chiolerio A., Wearable electronics and smart textiles: a critical review. Sensors, 2014, Jul. 7, 2014: 11957-92.
Redd CB, Bamberg S.J., A wireless sensory feedback device for real-time gait feedback and training. IEEE/ASME: Transactions on Mechatronics: Jun. 17, 2012 (3): 425-33.

\* cited by examiner

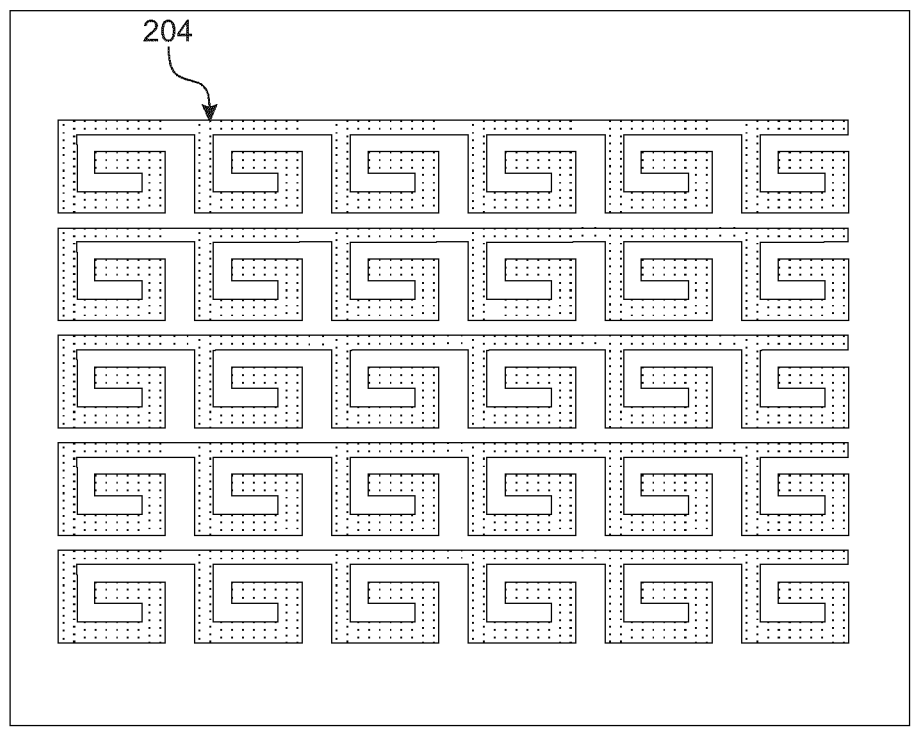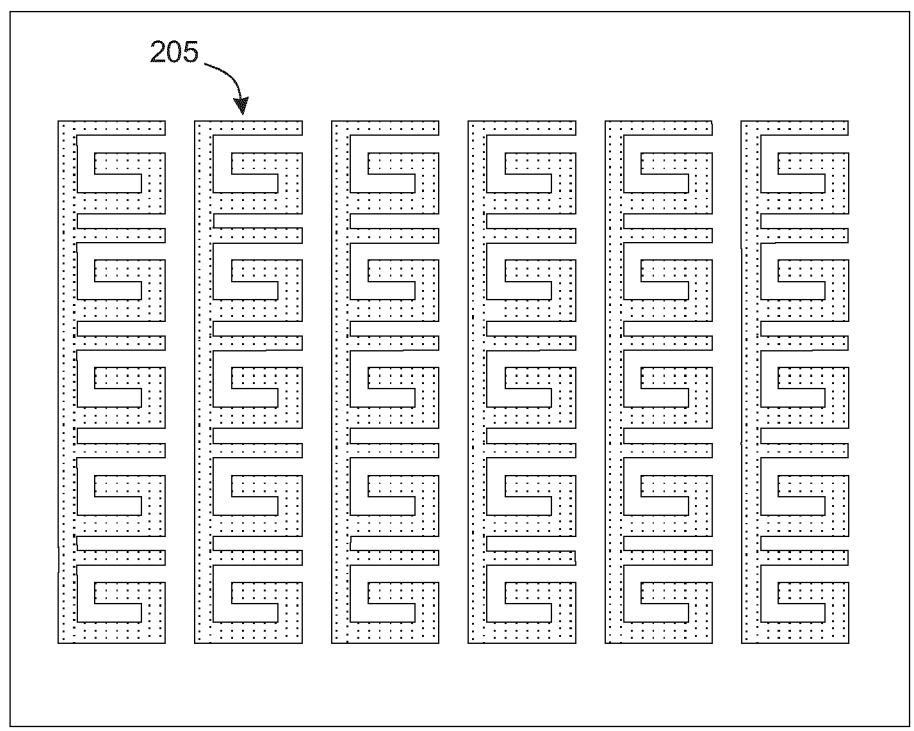
FIGURE 2D

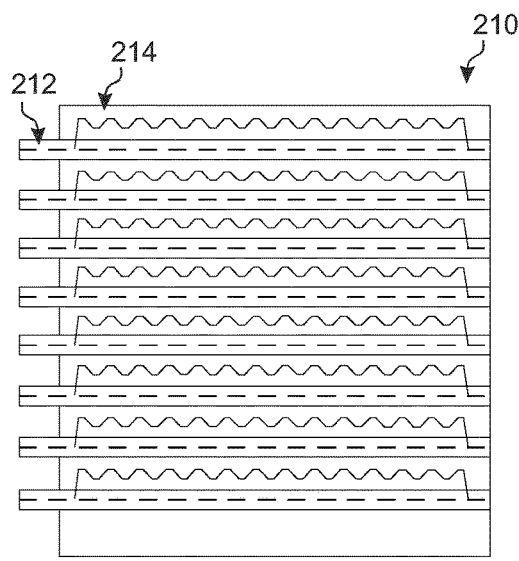
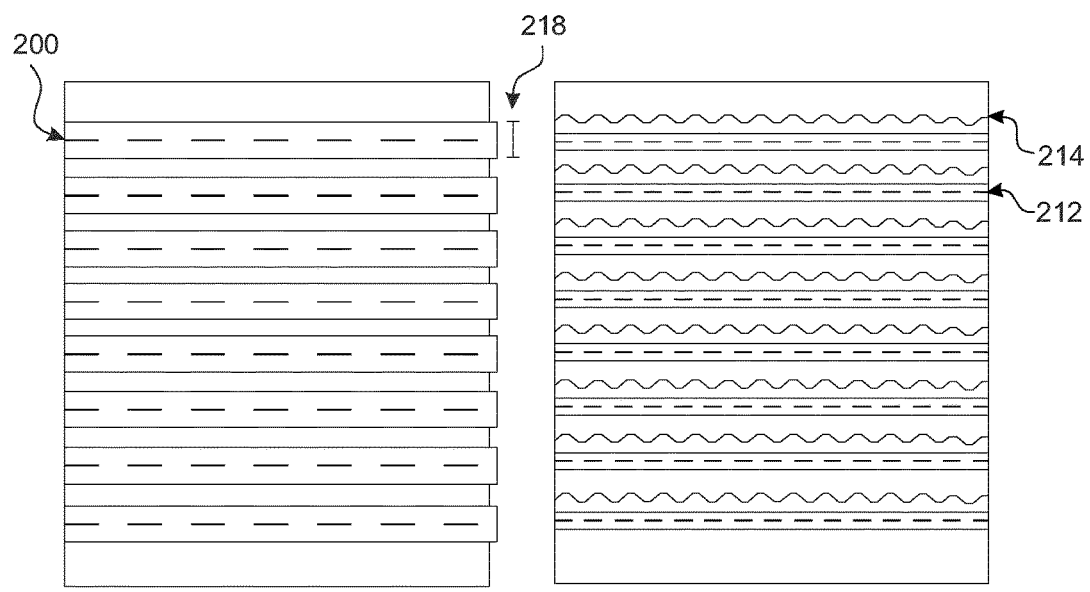
FIGURE 2E

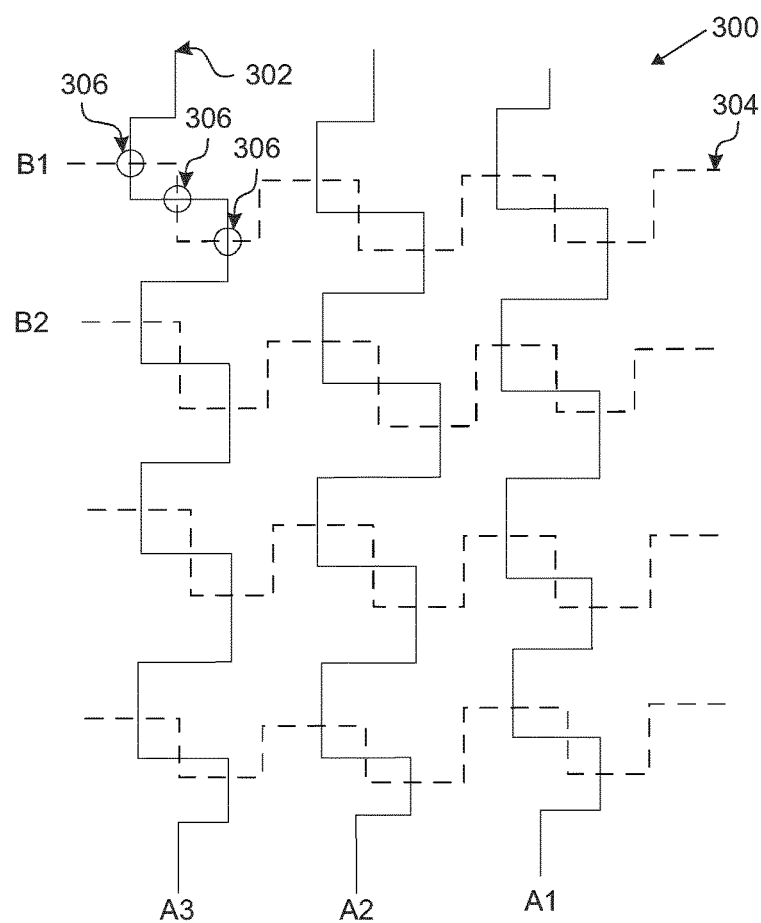
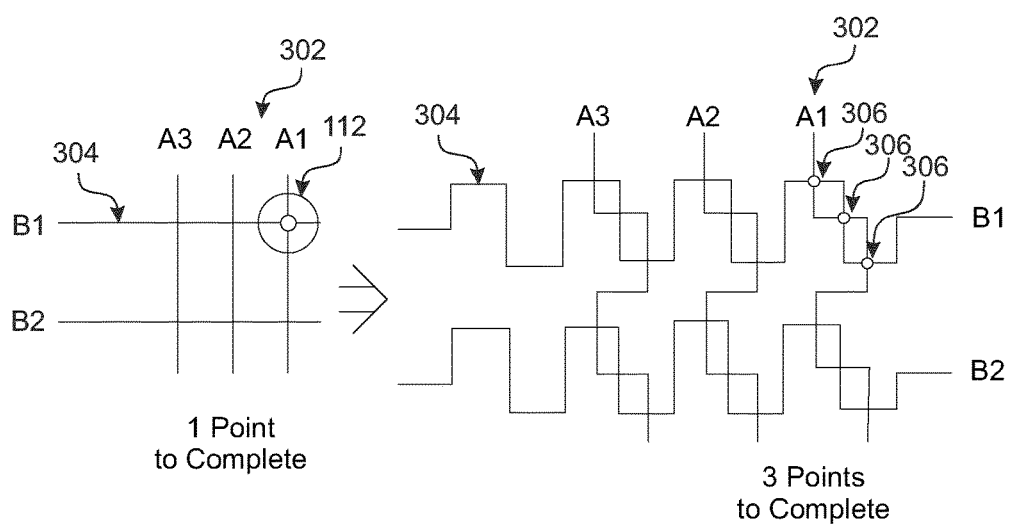
FIGURE 3

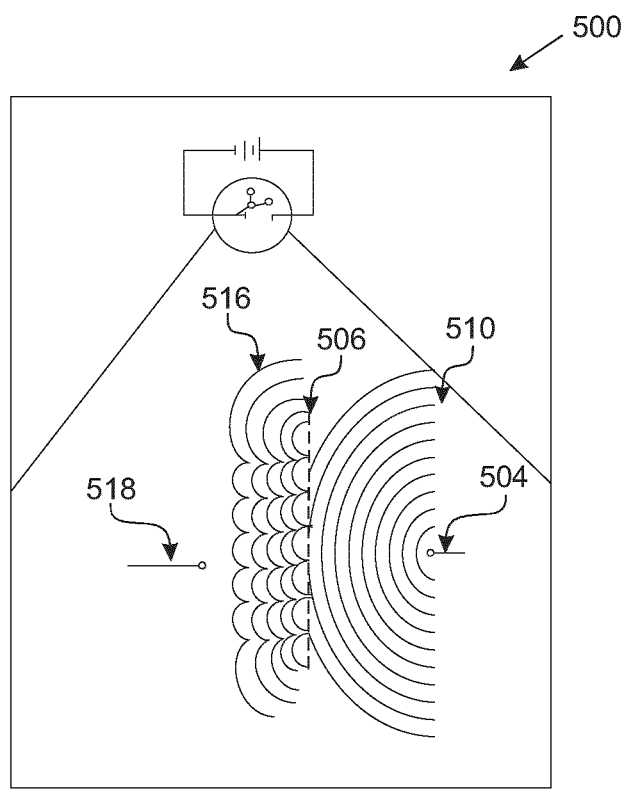
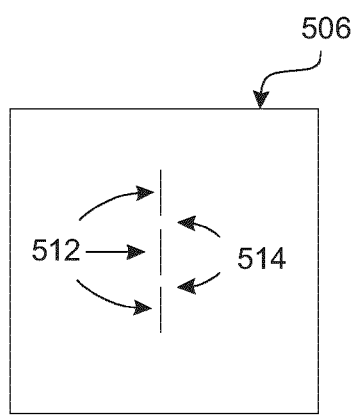
FIGURE 5A

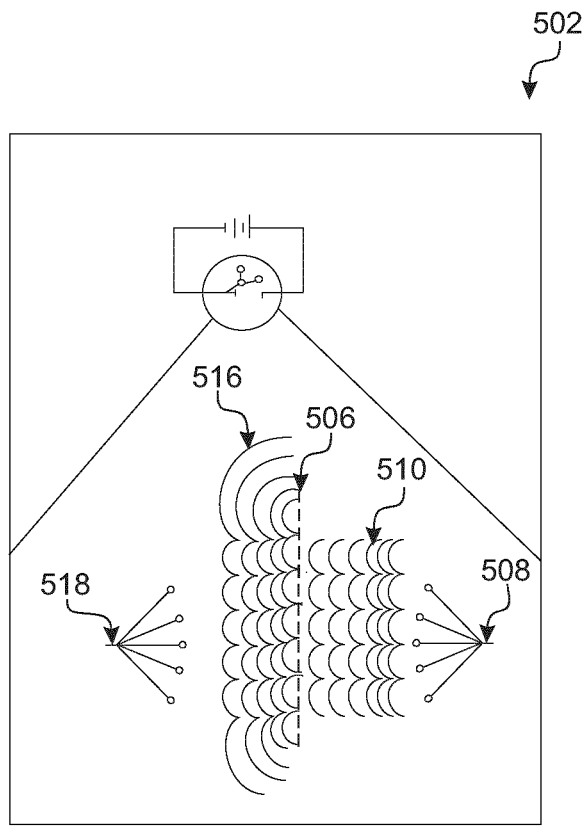
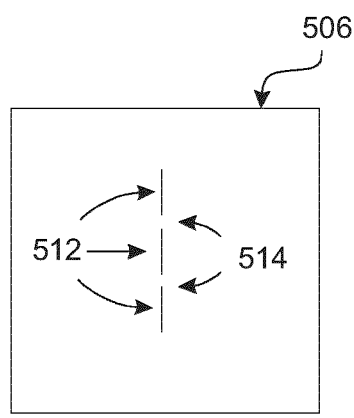
FIGURE 5B

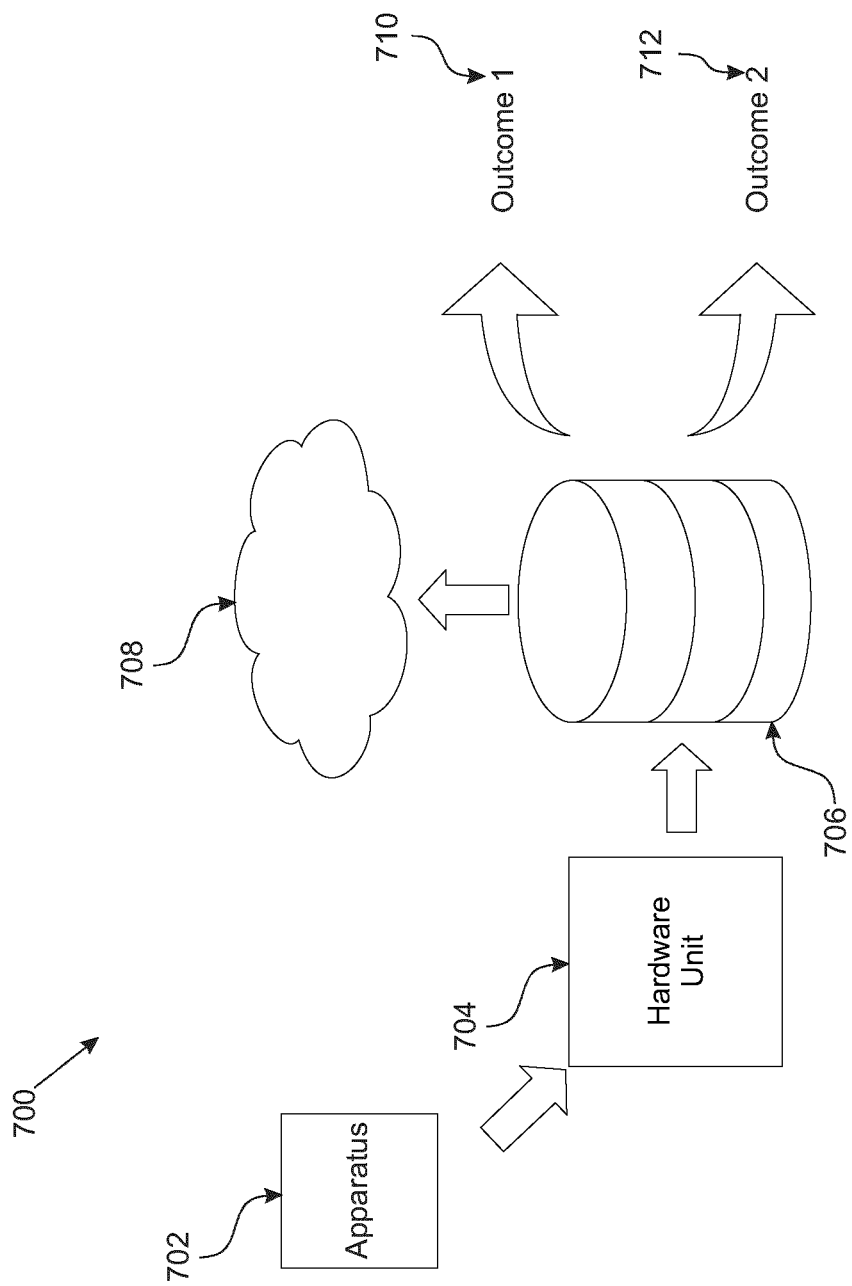

FLEXIBLE CONDUCTIVE APPARATUS AND SYSTEMS FOR DETECTING PRESSURE

CROSS-REFERENCE

This application is a U.S. nationalization under 35 U.S.C. § 371 of International Application No. PCT/CA2017/051267 filed Oct. 24, 2017 which claims the benefit of priority to U.S. Provisional Patent Application No. 62/412,438 filed Oct. 25, 2016 entitled FLEXIBLE CONDUCTIVE APPARATUS AND SYSTEMS FOR DETECTING PRESSURE, all the contents of which are herein incorporated by reference into the Detailed Description of Example Embodiments herein below.

TECHNICAL FIELD

At least some example embodiments relate to the field of variable pressure sensors and functional textile and, for example, to conductive apparatus and systems for detecting external force.

BACKGROUND

The global emergence of new materials and conductive textiles is expanding the capabilities of electronics with the ability to be integrated seamlessly into existing environments. Smart sensors improved the capability for everyday objects as a source of collecting electronic information by way of a connected device to the digital world. With the advancement of electronics through smart textiles, these materials have been used in many settings to create different types of sensors to derive information from the surrounding environment of the electronic devices. These sensors generally require 3 layers which include 2 layers of conductive materials separated by a middle layer, no different than a conventional circuit with a power source, a load for resistance, and a path to ground. When current passes from the first conductive layer through the middle resistive layer to the second conductive layer, the middle resistive layer acts as a bridge connecting a circuit so that a presence or an absence of pressure can be detected.

Another example of smart sensing is a grid of capacitive elements to form a capacitive sensor that is configured to be used, in one example, to detect touch-input. The interactive textile can process the touch-input to generate signal information from light contact that is used in controlling various devices and generally determines input of binary signals as related to the speed of electricity to travel in completion of a circuit, and not variability in the amount of pressure or force applied from the touch at each intersection on the conductive grid.

Pressure sensors face challenges related to drift/creep of signals increasing from coming into contact or through wear over an extended period. Different calibration techniques vary including direct intervention for recalibration or through normalization techniques of the signal output.

Monitoring systems and methods used to monitor health in some methods of smart monitoring require a sensor or sensors with limited form factors to be placed underneath a mattress, an arrangement that is less accurate in detecting placement of objects, positioning, and movement. Since the sensor is placed underneath the mattress, weight from external environmental factors would be distributed and would result in biased signal output.

Additional difficulties with existing systems, conductive fabrics and textiles may be appreciated in view of the Detailed Description of Example Embodiments, herein below.

SUMMARY

An example embodiment is a variable pressure sensor, and a flexible conductive apparatus, systems and methods for detecting pressure for using the variable pressure sensor. An example embodiment is an electrical apparatus that can act as a variable sensor or switch that can determine a higher degree of electrical signal range using only two electrical connections by manipulating the path of electricity and increasing the amount of surface area contact and/or number of contact points at each intersection that comprises of a single sensing element. For example, a light switch comprising of two electrical connections has generally the limited ability of producing an electrical signal output of a light being on or off when the circuit is closed or open. For a light switch to have dimming capability, an additional component such as a potentiometer or a variable resistor is required to provide variability of the electrical signals to control the varying brightness of a light. This is one example embodiment of a light dimming switch that can now be made using only two components of an electrical connection rather than the conventional setup of two electrical connections being limited to controlling a light being on or off.

An example embodiment of the system also comprises a sensor that can remain in electrical contact and change voltage output signal corresponding to the amount of force or pressure applied using two conductive elements, including against a non-compressible surface (or a surface that is sufficiently rigid and low elasticity so as to be perceived to be non-compressible) without bending or stretching of the apparatus. In this system, challenges related to sensor drift and creep can be diverted through power dispersion while the conductive paths remain in constant electrical contact, which is also beneficial to be applied in environments with changing form factors of the apparatus. Sensitivity can also be modified in the system by increasing the capture of energy not fully utilized as a result of natural resistance of conductive materials.

An example embodiment of the system also comprises a plurality of sensors that can determine a higher degree of electrical signal range at each intersecting point in a matrix design by allowing increased voltage supply at each intersecting point that comes into further contact with increased force and/or pressure applied to the apparatus.

An example embodiment of the system can take variable electrical signals and have a higher range of signal output, and be converted into higher validity of usable information. The usable information provides higher validity when used in applications related to healthcare and patient monitoring as an example of an embodiment of the apparatus. In accordance with an example embodiment, there is provided a system comprising of the flexible conductive apparatus described herein for generating a variable signal from each sensor area; a receiver for receiving the signals; a processor for processing the signals into processed data; a database for storing and analyzing the processed data, and an interface for communicating the processed data.

Example embodiments include applications of flexible sensors to be applied in multiple vertical applications through various embodiments that is not necessarily restricted to limitations due to flexibility of adopting different form factors while maintaining its sensing abilities, and being able to extract a higher range of electrical signals that can be converted into greater usable information that will benefit overall intended outcomes, while lowering overall costs from eliminating additional components to operate with the same level of functionality as previously used methods.

An example embodiment is variable conductive apparatus responsive to applied external force, comprising: a first conductive path that includes a first conductive surface; a second conductive path that includes a second conductive surface, a part of the second conductive surface having a conductive contact surface area with a part of the first conductive surface when there is no applied external force, another part of the second conductive surface separate from another part of the first conductive surface when there is no applied external force, wherein the applied external force increases the conductive contact surface area between the first conductive surface and the second conductive surface resulting in an increase in conductivity between the first conductive surface and the second conductive surface.

Another example embodiment is a variable pressure sensor comprising the variable conductive apparatus; a power supply for providing power to the first conductive paths; and a detector for detecting a detectable signal from the second conductive paths in dependence of the conductivity of the variable conductive apparatuses.

Another example embodiment is a sensor sheet comprising one or more layers and a plurality of sensors, each of the sensors comprising the variable conductive apparatus; a power supply for providing power to the first conductive paths; and a detector for detecting a detectable signal from the second conductive paths in dependence of the conductivity of the variable conductive apparatuses.

Another example embodiment is a system for monitoring external force comprising: a power supply; one or more variable pressure sensors, each comprising the variable conductive apparatus for receiving power from the power supply; a detector for detecting a detectable signal from the variable conductive apparatuses in dependence of the conductivity of the variable conductive apparatuses; a processor for processing the detectable signal into external force data, and for sending the external force data to a database or a server for storing and analyzing of the external force data; and an output device controlled by the processor to communicate an output in response to the detectable signal or the analyzed external force data.

Another example embodiment is a method of monitoring movement using the system, the method comprising: determining a baseline external force value when there is no external force applied to the variable conductive apparatus; obtaining signals having values above the baseline external force value; calculating differences between the obtained signals and the baseline external force value; and identifying one or more signals having differences greater than a difference threshold; outputting information to the output device based on said identifying when the one or more signals having differences greater than the difference threshold.

In some example embodiments, the system may be used for monitoring breathing of a subject, for monitoring heart rate of a subject, for monitoring movement of a subject, for monitoring and tracking location of a subject, for monitoring pressure level in a compression instrument, for monitoring pressure level in a compression instrument tourniquet, in a shelf for monitoring inventory levels, or in artificial exterior skin for providing a sense of touch to a robotic component.

BRIEF DESCRIPTION OF THE FIGURES

A detailed description of the example embodiments is provided herein below by way of example only and with reference to the following drawings, in which:

FIGS. 2A, 2B, 2C, 2D, 2E and 2F show examples of repeating pattern units for a conductive path.

FIG. 3 shows by way of an example embodiment in a matrix format, where a setup requiring multiple points of contact to make complete electrical connection such that reaching a maximum electrical signal will result from all points coming into contact.

FIGS. 5A and 5B show example diagrams of measuring electrical signal variance while the apparatus remains in constant electrical contact.

FIG. 7 shows an embodiment of a system incorporating a flexible conductive apparatus as a mat or a functional bed sheet health monitoring device, a hardware unit, a database, and a cloud server.

Similar reference numerals may be used in different figures to denote similar components.

DETAILED DESCRIPTION OF EXAMPLE EMBODIMENTS

In this specification, the term "force" and "pressure" are referring to the same notion of an intentional and unintentional interaction with an apparatus, and may be used interchangeably as applicable.

Sensors and switches have been used to understand information with regards to surrounding environments, or to control the outcome of an intended task. More information provides greater understanding, which normally results in greater amounts of sensors being added to increase understanding of further information at a higher degree. The basic fundamentals of electronic sensors are devices that determines electrical signals that are transformed into meaningful output that is used for a specific purpose or outcome. An example embodiment is a flexible conductive apparatus and systems for detecting pressure.

As individual sensors each require a minimum of two electrical connections in order to function, increasing the amount of sensors would result in doubling the amount of electrical connections for each additional sensor added. The purpose of adding further sensors is to have a greater understanding of external factors towards the intended purpose. An example, one sensor may be used to determine presence of an object but would provide limited information. To understand greater information such as the amount of pressure being applied by the presence of the object, additional sensors may be added.

Figure 1:
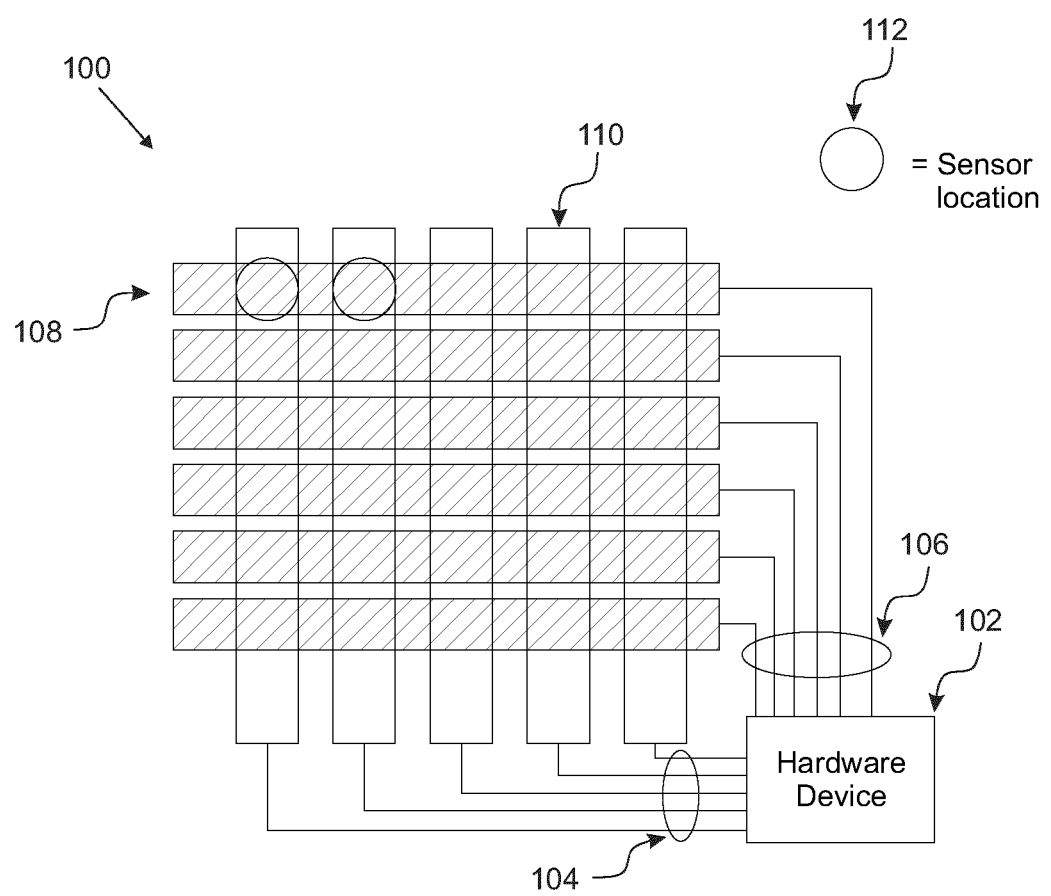
FIG. 1 shows an example pattern of overlapping first and second conductive paths for an embodiment of a flexible conductive apparatus, forming sensor areas at each intersecting points

A method and system of having increased amount of sensors while minimizing electrical connections per sensor is having the electrical connections in a matrix setup with a first and second conductive path intersecting, yielding a plurality of sensor areas at each intersection of the first and second conductive paths as shown in FIG. 1. In FIG. 1, an example system 100 of a flexible apparatus and system for detecting pressure is illustrated. An electronic controller 102 directs electrical current along conductive paths, conductive path 106 to second conductive path 108 leading in one direction, and conductive path 104 to first conductive path 110 leading in a direction perpendicular to conductive path 108, thereby creating a sensor at each intersecting point 112. Conductive textile strips define conductive paths 108 and 110 are an example embodiment used in a grid where each intersecting point determines the surface coverage of the sensing area 112. The sensing area 112 can be adjusted to cover less surface area coverage by reducing the sizes of the conductive textiles that define conductive paths 108 and 110. At each sensing area 112, the conductive paths 108 and 110 can include respective exposed conductive surfaces at each sensing area 112. Conductive paths 108 and 110 can be defined by other conductive elements in other example embodiments.

Figure 2A:
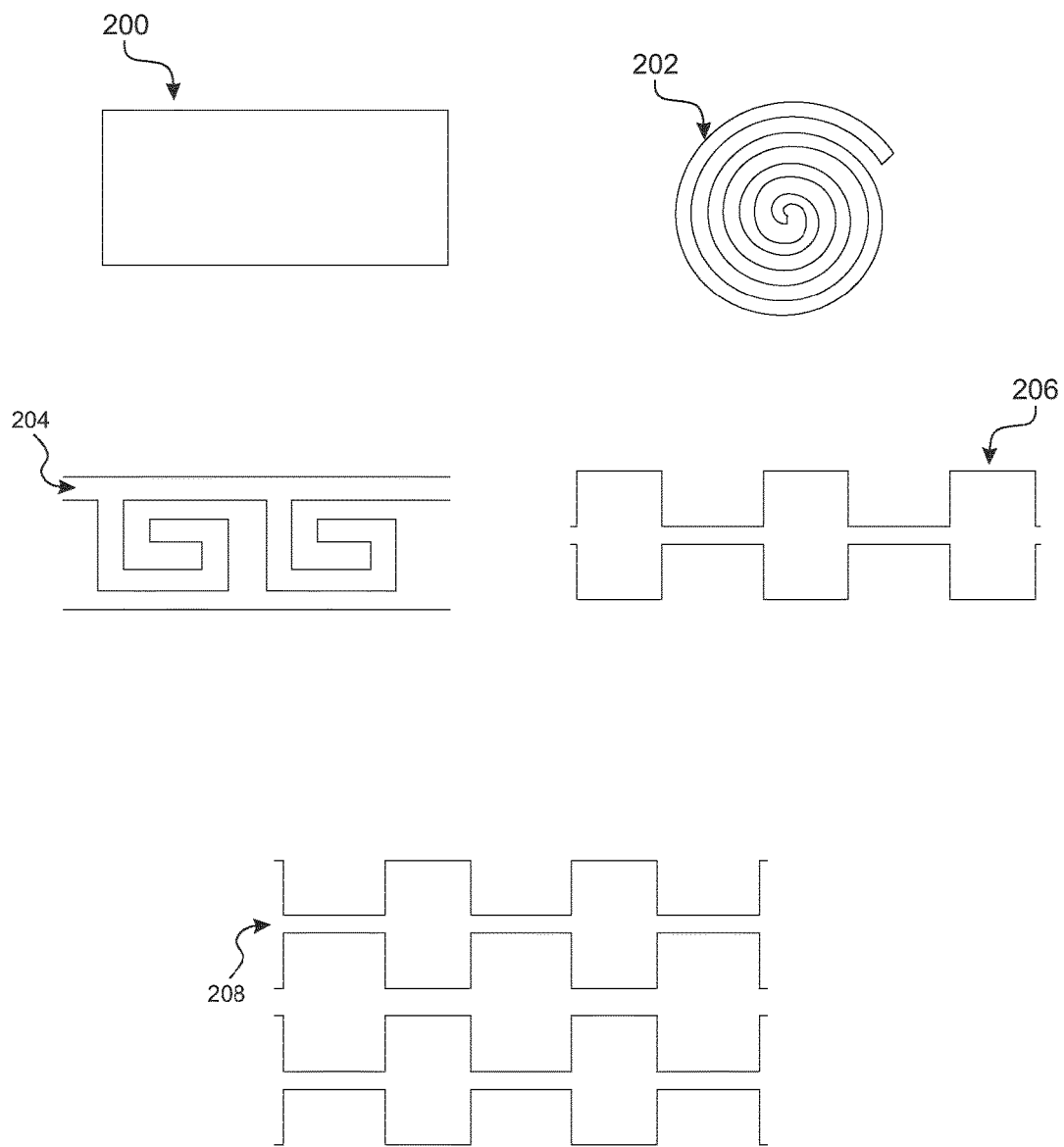

FIG. 2A illustrates different patterns that can be used as examples, where efficiency can be improved with a reduction of materials used. A conductive textile strip 200 as an example can be utilized more efficiently by using less materials and accomplish the same intended outcome or effective sensor coverage area. A spiral pattern 202 is an example of a circle that could be split and divided into two equal parts while covering the same effective area of detectability with half the amount of material, for example.

An example is demonstrated with one conductive textile strip 200 being divided efficiently using the spiral concept into two equal parts 204 using half the amount of materials to cover the same effective area of detectability in an embodiment demonstrated in conductive paths 108 and 110. A further demonstration of a conductive textile strip 200 being divided efficiently is 206 with less of the conductive textile material in gaps that may be placed on a grid where there is no intersecting conductive textile material, where the area with greater amounts of the conductive textile materials may be placed at intersecting points for conductive paths 108 and 110 to maximize surface area to increase the sensor area coverage. A conductive textile strip 200 may be divided for efficiency in the example 206 through the example demonstration pattern 208.

An illustration of an example embodiment of a setup using the conductive textile strip 200 divided for efficiency 204 is demonstrated. An illustration of an example embodiment of a setup using the conductive textile strip 200 divided for efficiency pattern 206 and pattern 208 is demonstrated. An illustration of an example embodiment of a setup using the conductive textile strip 200 on second conductive path 108 and overlap of a conductive textile strip 204 on first conductive path 110 is demonstrated.

Figure 2B:
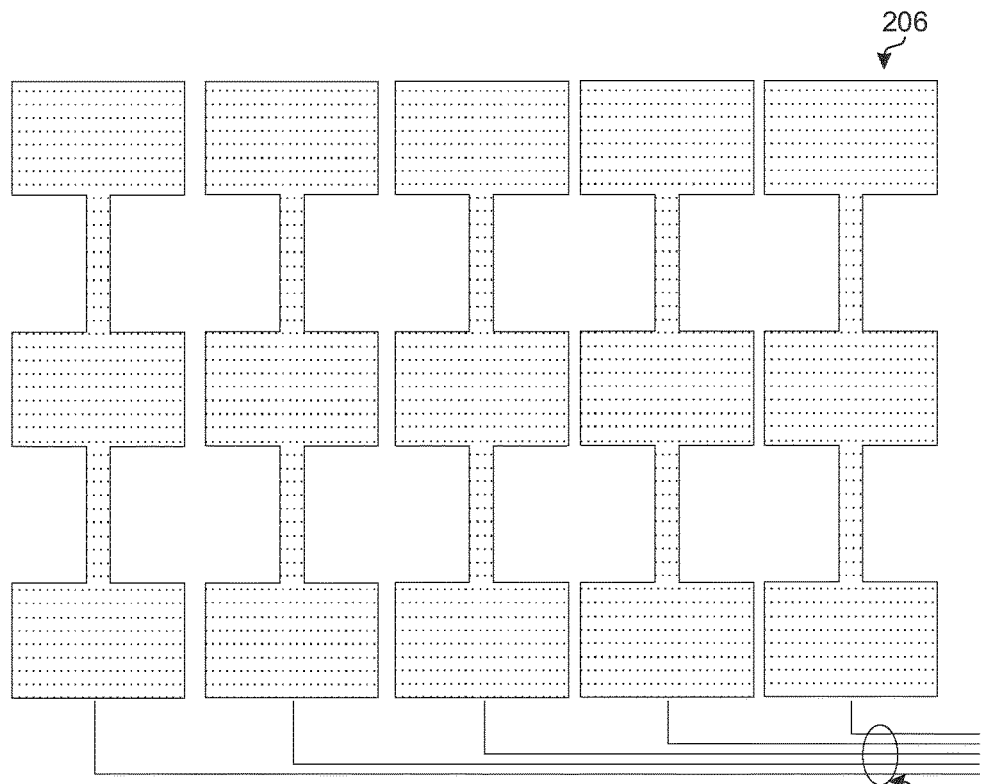

FIG. 2B illustrates an example conductive strip 200 that is divided with a design pattern 206 for efficiency to cover same effective surface area coverage at intersecting points that create a sensor location 112, with using less materials in the empty gaps where illustrated in the pattern 206.

Figure 2C:
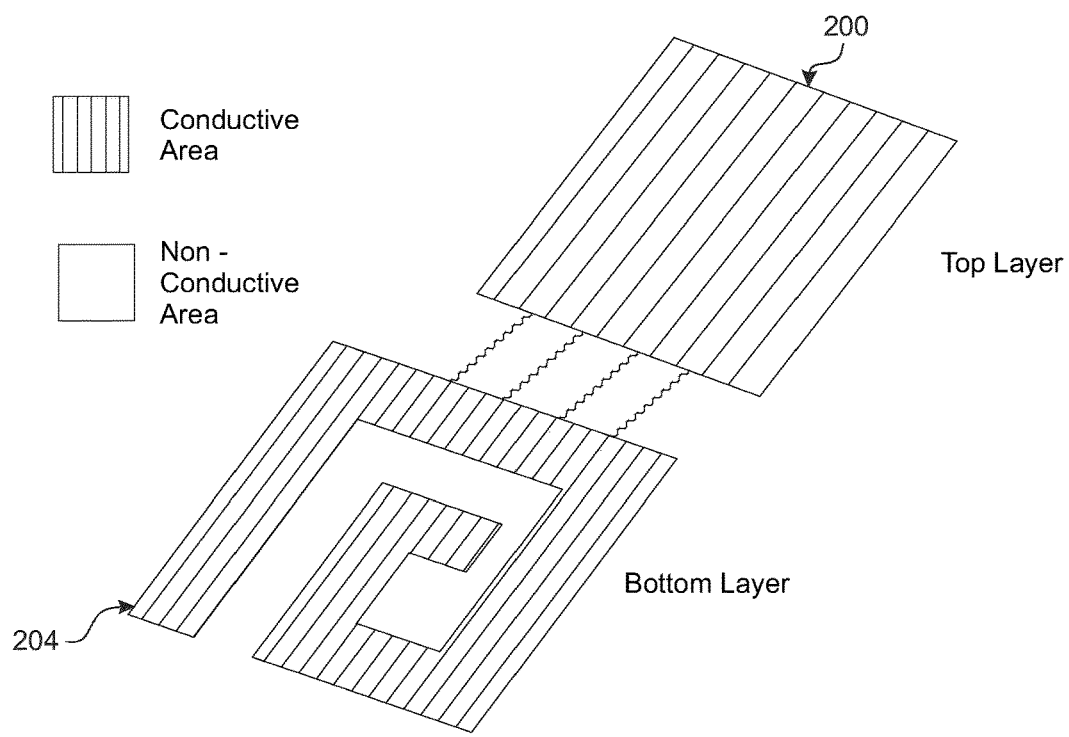

FIG. 2C illustrates an example conductive strip 200 that is used on one conductive path, and a textile strip that is divided using half the material 204 for a second conductive path, while covering the same surface area as the first conductive path 200.

FIG. 2D illustrates an example of a conductive strip 200 that is divided and used for first conductive path 204 leading in one direction and second conductive path 205 leading in a perpendicular direction to 204, demonstrating that the same surface area coverage could be achieved using half the materials.

FIG. 2E illustrates an example using conductive fabrics 212 and conductive threads 214 for a more efficient method of covering greater surface area of sensing using less materials for one conductive path, as compared 218 to a conductive strip 200.

Figure 2F:
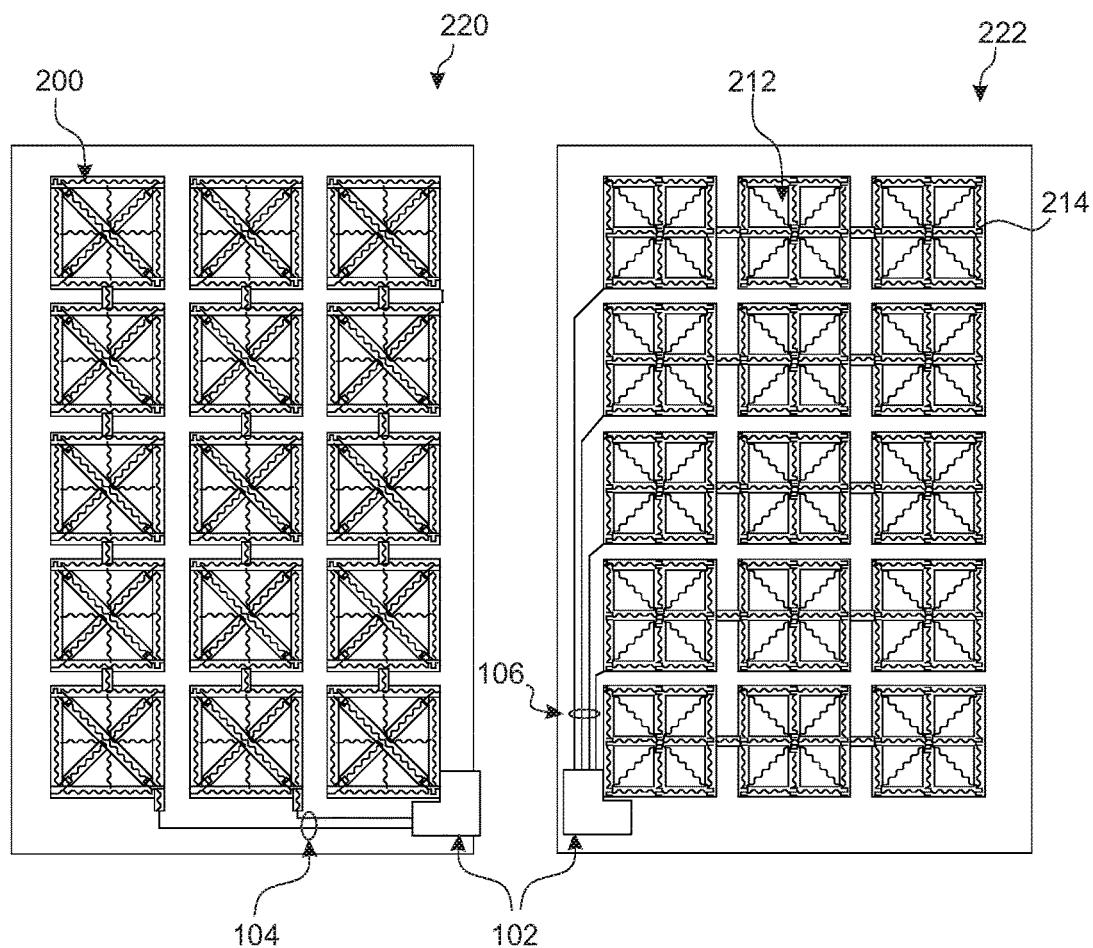

FIG. 2F illustrates an example using conductive fabrics 212 and conductive threads 214 in a second example conductive path design 220 and 222 using conductive fabrics and threads for a more efficient method of covering greater surface area of sensing using less materials.

Generally a conductive path of a current carrying conductor has consistent voltage wherein when used alone for a single circuit or in a matrix would yield a result of sensing from two points coming into contact determining minimal electrical signal variance such as being on or off. There is the ability of determining signal variance based on the amount of force or pressure applied at each intersecting point that creates a sensor by increasing the contact points at each intersection as illustrated in FIG. 3. This illustration is an example embodiment 300 of a matrix setup in an intersecting grid 302 and 304 like that of conductive textile strips defining conductive paths 110 and 108.

For example, a cross-sectional area of a conductive material is proportional to the resistance. For example, the resistance R of any material with a uniform cross-sectional area A and length L is directly proportional to the length and inversely proportional to its cross-sectional area. In mathematical form, $R=\rho*L/A$, wherein the Greek letter rho ($\rho$) is known as the resistivity of the material. Resistivity is a physical property of the material and is measured in ohm-meters.

For example, liquids flow through large-diameter pipes easier than they do through small-diameter pipes. The same general principle holds for the flow of electrons through conductors. The broader the cross-sectional area (thickness) of the conductor, the more room for electrons to flow, and consequently, the greater the conductance and the easier it is for flow to occur (e.g. less resistance).

By a similar principal, the amount of surface area contact between the first conductive path 110 and second conductive path 108 determines the amount of resistance or conductivity there between. When a DC power source or charge is applied to the first conductive path 110, a resultant voltage signal is detectable from the second conductive path 108.

Conductive materials have varying levels of conductivity and electrical resistance. Utilizing the physical properties of natural resistance to the benefit of electrical sensing, variable signal detection can be performed through corresponding with the amount of points coming into contact at each intersecting point creating a sensor area 112 as illustrated in FIG. 3. Each contact point 306 comprises an exposed surface area of each of the conductive paths. An example being if one of three of the points 306 come into contact, the effective resistance will be greater and only approximately ⅓ of the voltage signal will be detected. As illustrated, an example embodiment of a conductive path design in a matrix setup 302 and 304 requiring multiple points of contact 306 to make connection at each intersection of first conductive path 110 and second conductive path 108 will result in such that reaching a maximum electrical signal at each intersecting sensor area 112 requires all points 306 (three in this example) being in contact, and the voltage signal detection will correspond with the amount of points that are in contact with each of the corresponding points 306 in the individual sensor area 112.

Figure 4A:
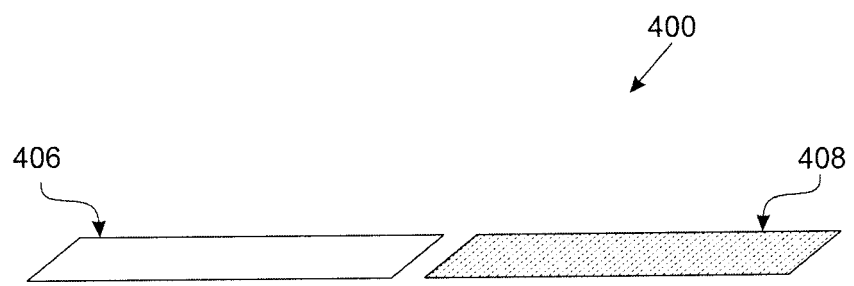
FIGS. 4A, 4B, and 4C shows an example embodiment of measuring higher electrical signal variance with first conductive path overlapping second conductive path to increase surface area contact.
Figure 4B:
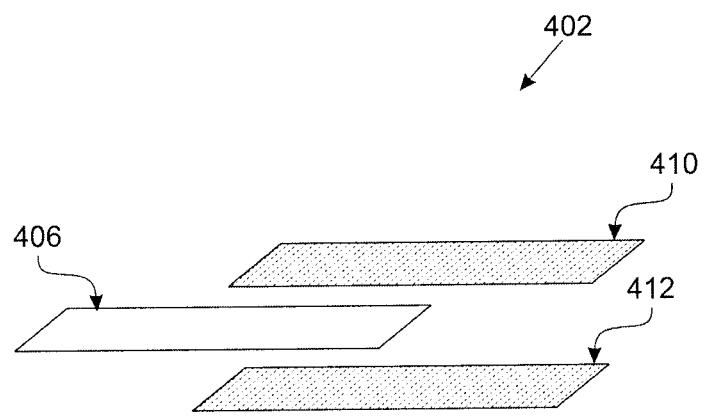
Figure 4C:
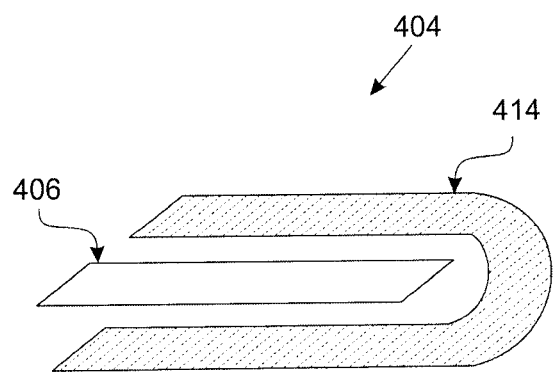

FIG. 4 illustrates examples of conductive path designs beginning with a first design 400 where a first conductive path 406 input and a second conductive path 408 output is demonstrating a connection, in an example being a circuit, that results in a completion of a circuit.

An example of a second conductive path design 402 is illustrated with a first conductive path 406 input, a second conductive path 410 output, and a third conductive path 412 output whereby if the first conductive path 406 has an input electrical signal, the second 410 and third 412 conductive paths coming into contact with the first conductive path 406 will result in a higher electrical signal output due to greater surface area contact, similar to increasing a diameter of a wire to increase conductivity and decrease resistance. This may be beneficial to increase sensitivity and data range in sensor applications, but for data range would require the sum of the data output of the circuit of conductive path 406 and conductive path 410, and the circuit output of conductive path 406 and conductive path 412. By increasing the amount of contact surface area of the second conductive path 410 and third conductive path 412 coming into contact with the first conductive path 406, similar to increased contact points 306, will allow an increase of voltage signal due to the greater conductivity and lower resistance at the contact points.

An example of a third conductive path design 404 illustrates an example of a first conductive path 406 input and a second conductive path 414 output, where increasing the amount of contact surface area of the second conductive path 414 coming into contact with the first conductive path 406, similar to increased contact points 306, allows an increase of resultant voltage potential and extracting unspent energy due to increased conductivity and decreasing resistance. This design 404 may be beneficial to increase sensitivity and data range in sensor applications, and for data range where it also improves efficiency over conductive path design 402 as it reduces the amount of electrical connections required whereby a second conductive path 414 combines two required connections of a second 410 and third 412 conductive path into one conductive path 414.

As even conductive materials have some natural resistance, increasing cross-sectional area contact size is to provide additional conductive paths for the electricity to flow over greater distances. Similar to this is increasing the amount of contact points 306 correlating to each intersecting point 112 from the first and second conductive paths 110 and 108 coming into contact to create a greater signal output, and increasing the amount of surface area contact 414 correlating to the first conductive path 406. More contact points increases conductivity between the first and second conductive paths 110 and 108. Through this aspect of greater surface area contact 404 and multiple points of contact 306 at each intersecting point, voltage potential increases at each additional contact point with resistance changing as a result of the corresponding applied force.

Sensor drift and creep is a common occurrence for pressure sensors over periods of time. In situations where there is constant contact, in an example embodiment, electrical paths can be diverted through dispersion to reduce strain on the conductive paths in order to minimize wear from constant electrical contact. FIG. 5A illustrates a diagram of a circuit 500 with the effect of a conductor 504 with an electrical path that is distributed by conduction layer 510. Conductive layer 510 is, for example, a conductive material or a fabric with many densely packed conductive threads. The electrical path through the conductive layer 510 is configured to come into contact with a load, which will be referred by way of this example as a resistive layer 506 that contains distributed conductive threads 512 spaced out and separated by non-conductive threads 514, and the electrical path is then further distributed by conduction layer 516 and continues to the output conductor 518 providing an electrical signal output that is detectable. Electrical path distribution by conduction layer 510 through a resistive layer 506 is dispersed with distributed electrical contact through conductive threads 512 and separation with non-conductive threads 514 through insulation by the non-conductive threads and insulation through natural air separation. To lessen electrical resistance and increase electrical signal conductance, further contact through external environments, by way of example of pressure being applied, will compress input conductor 504, resistive layer 506, and output conductor 518 together as if all combined elements were one larger single conductor, and result in an increase of electrical signal conductance as more surface area contacts are made as a result of the applied pressure. When full pressure is applied, conductance along input conductor 504, resistive layer 506, and output conductor 518 is maximized and the detectable electrical signal from output conductor 518 is at maximum, e.g. on or about maximum 5 V or a maximum calibrated value of 1024.

FIG. 5B further illustrates a diagram of a circuit 502 with the effect of a conductor 508 that demonstrates the ability to detect signal variance by increasing the amount of different input paths of a conductor 508 with electrical path distribution by conduction layer 510 that is distributed through the middle resistive layer 506 and continues with further distribution by conduction layer 516 through conductor 518, where electrical signal output will vary correlating to the amount of input conductor 508, resistive layer 506, and output conductor 518 that are in conductive contact. It follows the previous example FIG. 5A that the increasing surface area of points of contact of all combined elements will result in acting as a single conductor having greater conductance and lower resistance, resulting in an outcome of a greater electrical signal output. When full pressure is applied, for example, conductance along input conductor 508, resistive layer 506, and output conductor 518 is maximized and the detectable electrical signal from output conductor 518 is at maximum, e.g. on or about maximum 5 V or a maximum calibrated value of 1024.

Example embodiments of systems and methods demonstrated in FIGS. 3, 4, 5A, and 5B are also beneficial to be used in printed circuit board and electronic chips to allow greater signal variance to increase the functioning capability of integrated circuits that are generally limited to performing binary tasks.

Figure 6A:
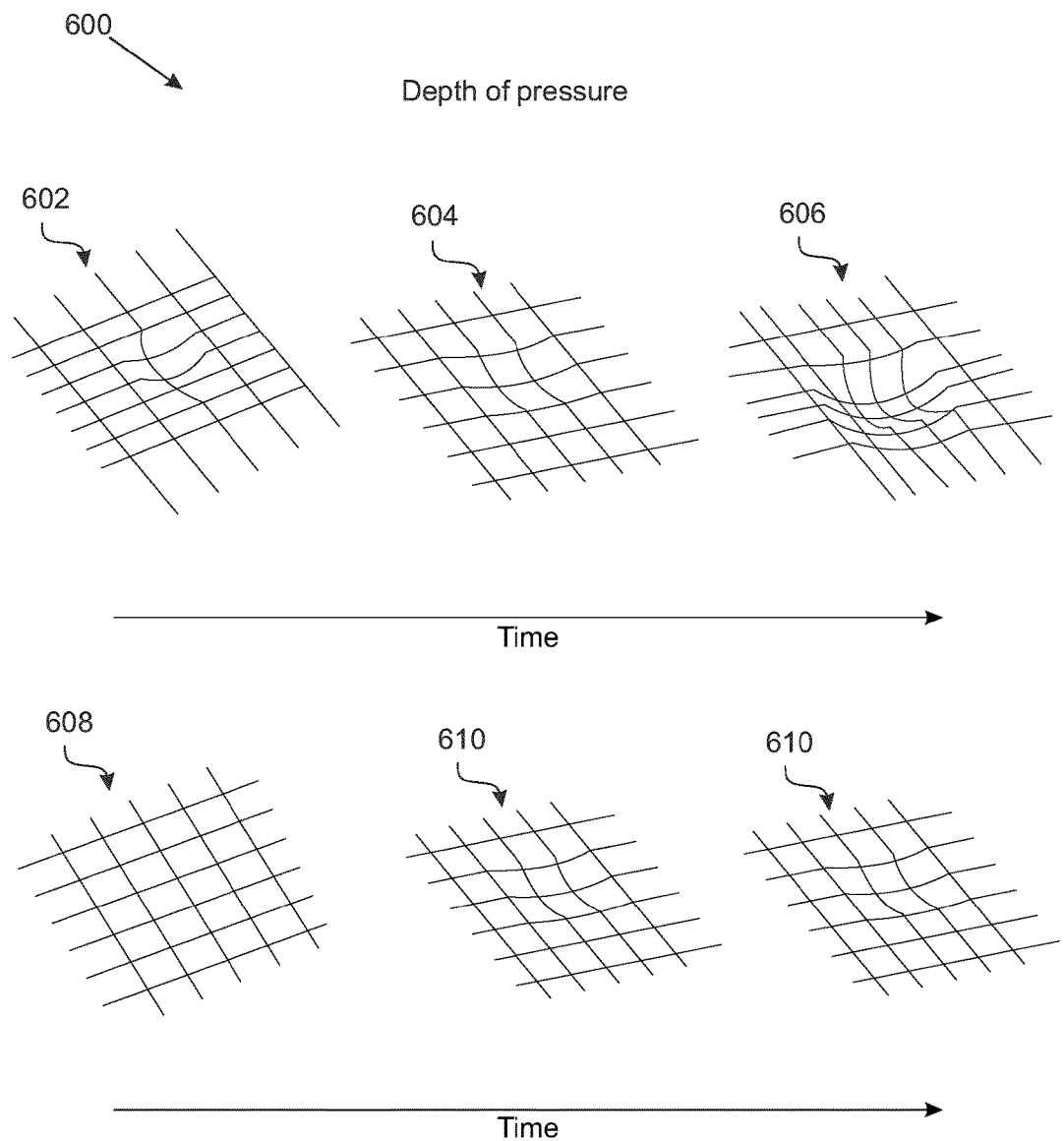
FIG. 6A shows representative illustrations of the distortions that the flexible conductive apparatus undergoes when pressure/force is applied.

FIG. 6A illustrates distortions of the flexible conductive apparatus by way of demonstrating different forces of pressure applied on the apparatus over time 600. When pressure is applied on the apparatus 602, represented is a visual demonstration as what is detectable with the apparatus. As further pressure is applied on the apparatus, there is further distortion 604 with the ability to detect increasing amounts of pressure 606 on the apparatus, thereby representing the ability for the apparatus to determine depth and volume corresponding to the amount of pressure applied. When there is no pressure applied 608, and then consistent pressure is applied as could be due to by way of example a still object over time, the detection of amount of pressure remains stable 610.

Figure 6B:
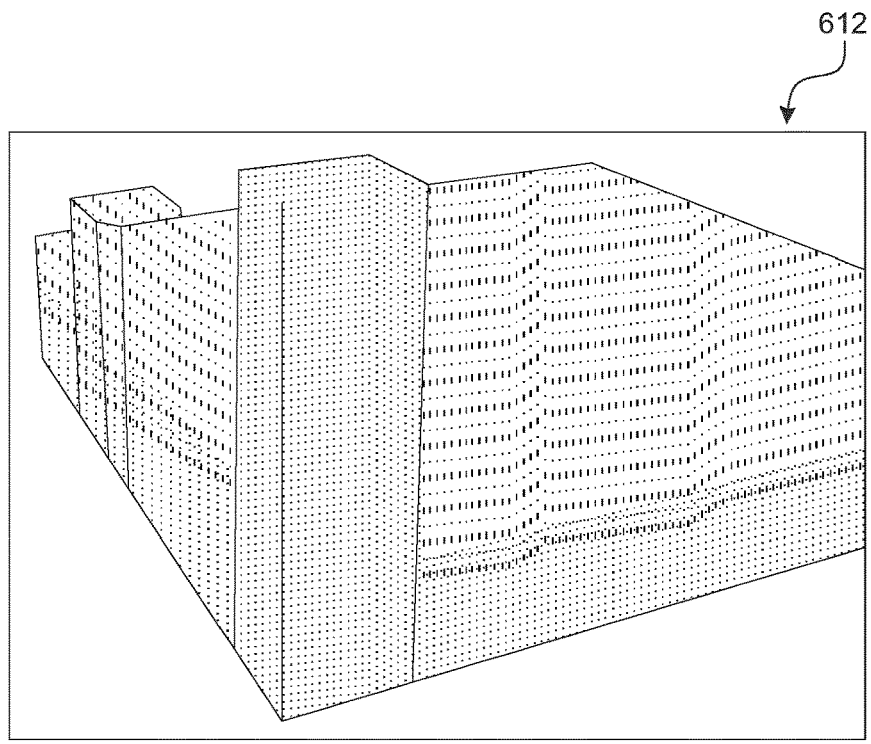
FIG. 6B shows an example of the flexible conductive apparatus in three-dimensional imaging.

FIG. 6B illustrates distortion of the flexible conductive apparatus by way of demonstrating different forces correlating to the amount of pressure applied on a three dimensional graph 612 with the highest amount of pressure applied at the corner as represented in the figure, demonstrating the ability for detecting three-dimensional mapping, location, and weight differential throughout the apparatus.

Figure 6C:
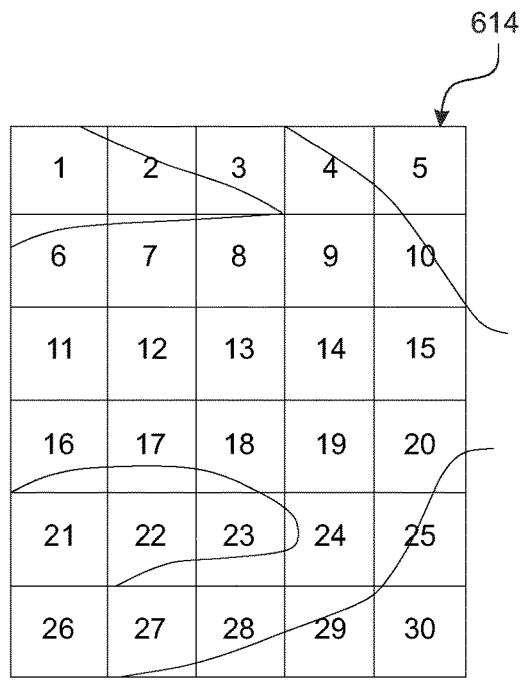
FIG. 6C shows an outline of a two dimensional mapping of a body lying on the flexible conductive apparatus.

FIG. 6C illustrates a two-dimensional mapping, with an outline of the body, through determining active sensors in one example embodiment of controlled testing of the flexible conductive apparatus as a health monitor application. In this example configuration, the flexible conductive apparatus system consisted of 30 sensors configured in a 5×6 matrix.

It will be demonstrated further, for applications in healthcare patient monitoring. Each individual sensor has the ability to detect depth and variations of pressure, where sensor regions can be segmented to determine active versus inactive sensors corresponding to applied pressure areas versus no pressure areas 614, and changes in pressure levels among the sensor areas. This is a beneficial outcome by demonstrating in an example of a human body that lays on a bed and rolls to their side or around to other parts of a bed, there will remain continuous output of electrical signals where the flexible conductive apparatus system is in contact with the body to provide continuous monitoring of a patient/user. An additional benefit is providing further indication of signal noise such as jumps or spikes of the electrical signal outputs, where the two-dimensional mapping will provide reference as to originating signal noise that may be attributed to movement on the flexible conductive apparatus.

FIG. 7 illustrates an example embodiment of a flexible conductive apparatus 702 in a monitoring system 700. The flexible conductive apparatus 702 outputs electrical signals to the hardware unit 704, that may process the signal information on the hardware unit 704 and/or transmit the raw electrical signal information to a database 706. The database 706 may then conduct further processing of information and/or transmit the information to a cloud server 708, for further analysis that may produce by way of example in this illustration one intended outcome 710, or an alternative intended outcome 712. Data stored in the database can be used for health analysis, as well as for customized output functions such as notifications and/or alerts.

Another example embodiment of a system incorporating a flexible conductive apparatus 702 for a monitoring system 700 is for a surface area detecting three dimensional mapping, location, and weight differential throughout the apparatus with data analysis that could be used for monitoring inventory levels or presence of inventory items on an intelligent shelving unit, for an automated process of inventory control as one potential outcome 710, and/or the pre-ordering process for restocking inventory as an alternative potential outcome 712. In an example embodiment, rather than a flexible supporting layer, a rigid material (e.g. low or non-perceivable flexibility) such as a shelf incorporates the variable pressure sensor, and the minor deformations in the rigid material are detectable.

The flexible conductive apparatus is connected to a hardware unit which includes a microcontroller, a processor, a single board computer that comprises a wireless and wired network capabilities, multiplexers, analog-digital converters, amplifiers, alerting device, speakers, buzzers, LEDs/LED strips, accelerometer, gyroscope, or combinations thereof. The conductive apparatus serves as a resistance for current to pass through.

In a matrix design, for example, one side of the electrical connections of a second conductive path 108 (e.g., rows) to the conductive apparatus serves as an input signals and is connected to one MUX whereas the other side of the connections of a first conductive path 110 (e.g., columns) serves as the output and is connected to the other MUX. The MUX is then interconnected to the other components in the hardware unit. Through multiplexing signals very rapidly, one side of the connections for the second conductive path 108 (input) is sending voltage and the other side first conductive path 110 (output) is reading signals and determining if any intersection between the column and row is pressed along with the amount of pressure is applied. As an analogy, the conductive apparatus serves as an array of piezo sensors and/or variable resistors that allows passage of current through to complete the circuit and output a signal. The amount of force and/or pressure applied dictates how much current is passing through with greater pressure allowing more current flow to output a greater electrical signal.

Pull-down resistors are included with the analog input signal to stabilize and improve the consistency of the values across all signals. Pull-up resistors are also included with the input signals in order to increase the range of sensitivity.

Figure 8A:
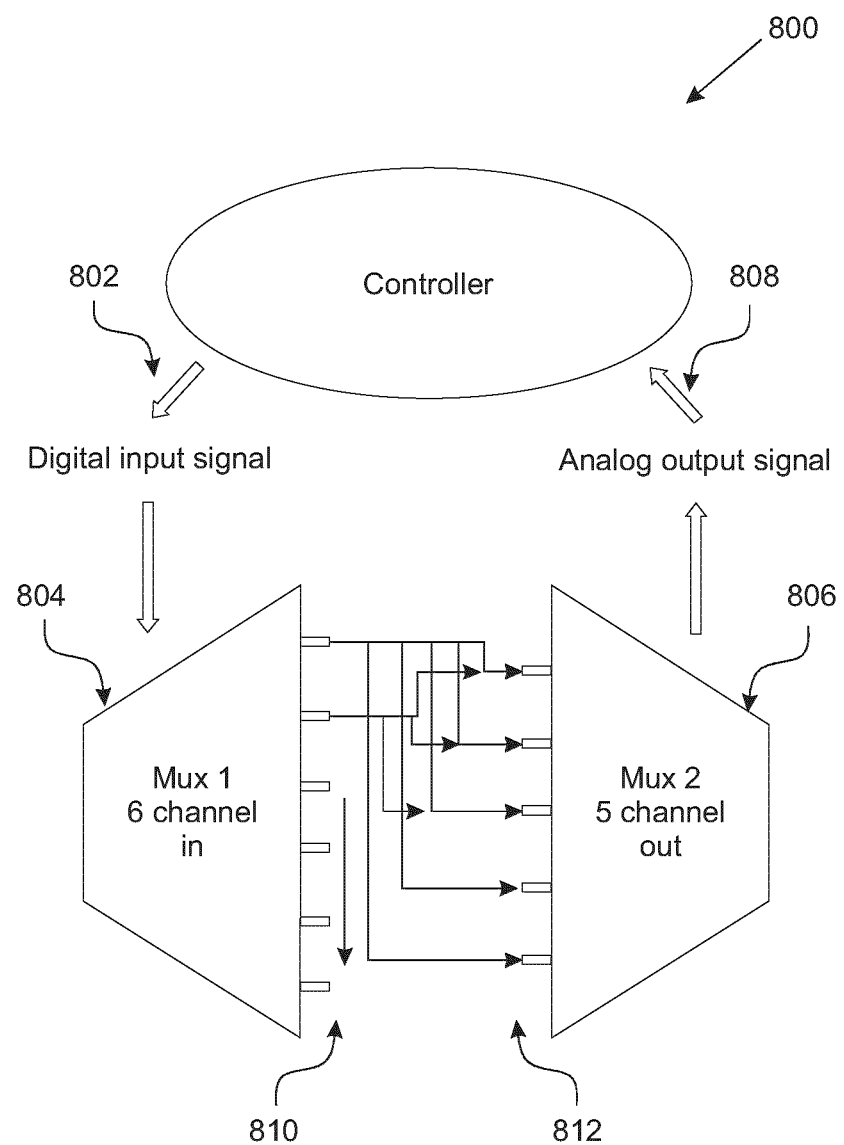
FIGS. 8A, 8B and 8C show an example of the conductive paths in a matrix grid, where the power signal is input into one multiplexer and the output signal is read from the other multiplexer, thereby being able to read multiple electrical signals with fewer connections for each sensor point.
Figure 8B:
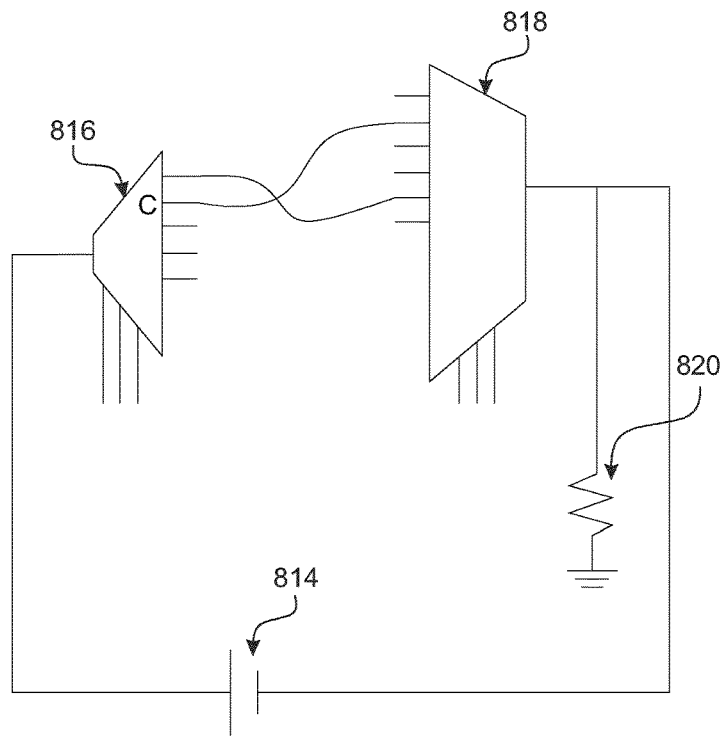
Figure 8C:
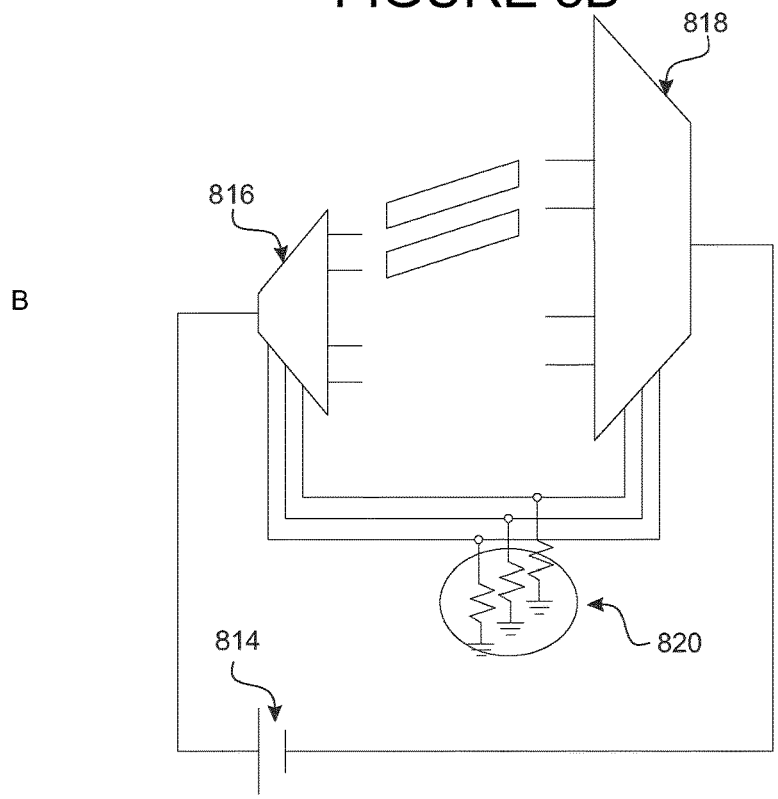

With the many applications the flexible conductive apparatus can be applied, FIGS. 8A, 8B and 8C illustrate the functioning of circuitry 800 that minimizes the electrical connections required by using a matrix setup that multiplexes electrical signals, while maintaining higher data range of output signals.

Example circuit setup using two multiplexers are illustrated in FIGS. 8A, 8B and 8C. Power is connected to multiplexers (MUX). In the example 800, two multiplexers take digital and/or analog inputs where the first conductive path 802 will input a single digital signal into MUX 804, and multiply the digital signals into the amount of combinations as in this example of 6 channel inputs 810, and be collected through a secondary MUX 806 that will receive multiple digital signals through the amounts of combinations as in this example of 5 channel outputs 812, thereby creating a 6×5 matrix outputting a combination of 30 sensors in this example. Between MUX 804 and MUX 806, there will be signal output of variable electrical signals corresponding to the amount of sensor areas coming into contact, along with the amount of pressure applied at each sensor area.

FIGS. 8B and 8C further illustrate the circuitry in an example setup with a power source 814, an input MUX 816, an output MUX 818, and pull-down resistors 820.

Functional textiles are useful in manufacturing instruments that can generate information from an input signal resulting from contact with the textile. Such instruments can detect the amount or variations of force/pressure applied and may also have a stimulus response built in. An example of an application of such an instrument is embedding a flexible conductive apparatus in accordance with an example embodiment into everyday furnishings such as couch lining, carpets, mats, flooring, or linen to detect when there is presence of a force/pressure applied. Such an application can be useful in monitoring behavior to create real-time information of the presence of individuals in a building or the location of an individual. It can also monitor if there is a fall, and continue monitoring while emergency responders are dispatched. All of these may be useful in monitoring, for example, Alzheimer or dementia patients, or in conserving energy by powering devices based on real-time information of the presence of individuals in a location.

Another example application involves embedding a flexible conductive apparatus in medical devices such as a compression instrument, bedding, or leads to monitor levels of pressure or changes in pressure arising from heart rate or pulses, or a body contact during inhalation and exhalation or other respiratory changes. This opens up the potential for future applications in general patient health monitoring without the need for any leads and/or attachments to the patient body.

Figure 9:
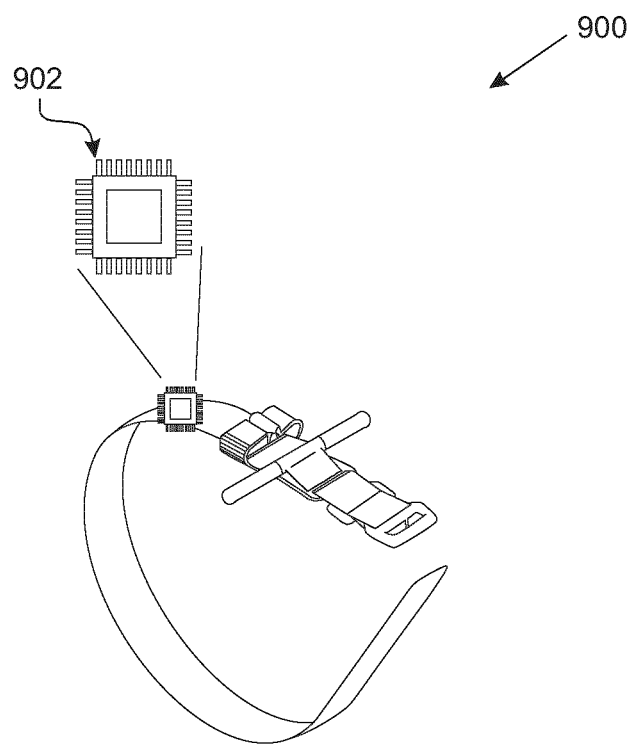
FIG. 9 shows an example embodiment of a flexible conductive apparatus system that can be attached to an existing device without alteration, to increase the efficiency for measuring such device outcomes as intended.

For example, illustrated in FIG. 9 is where a compression instrument tourniquet 900 is shown, where a tourniquet 900 when used requires a consistent amount of pressure to be applied and maintained on a body part to occlude blood vessels, preventing bleeding such as traumatic bleeding in emergency situations. This example embodiment demonstrates a flexible conductive apparatus system 902 that can be attached to existing devices such as the compression instrument tourniquet 900 to improve outcomes of providing continuous monitoring, rather than having to make alterations on the devices. The flexible conductive apparatus system 902 can comprise any of the described flexible conductive apparatus 702. This can be helpful in military applications or for emergency personnel who use combat application tourniquets (CAT) in situations where the monitoring of pressure is difficult to attend to in high-stress situations requiring CATs, and often when muscles contract, pressure from CATs require retightening to prevent further bleeding that would otherwise increase the risk of fatality. The flexibility of the conductive apparatus could be applied in any location or on any part of the body as it could take any form factor, and monitor applied pressure continuously and notify if there is a decrease in pressure that falls below a set parameter, alerting for the need for attending to, in order to maintain the required level of pressure. In addition, the apparatus could monitor the length of time of application of the tourniquet 900, where extended periods of time being applied may result in potential risks of amputation.

In example embodiments, beddings incorporating functional textiles can provide information regarding, for example, respiratory changes or length of time of complacency. While other devices require direct attachments to the body, the functional textiles of example embodiments maintain contact with the body while measuring changes in pressure and weight distribution from expansion and contraction of the body, and can be useful for long term research with events leading up to health outcomes, or alerting irregular breathing, or mitigating pressure ulcers from forming due to limited movements. Measuring vibrations emitted by pulses in the body using techniques such as ballistocardiography may be one method that could provide information regarding heart rate. One benefit of using such functional textiles is the replacement of conventional approaches to vital sign monitoring which requires leads and attachments to the body, and offers a non-invasive solution using a common everyday item such as a bed sheet that has been made into a functional device using functional textiles. It would also provide more accurate information with a consistent baseline comparison, by limiting user bias while using the example embodiment while asleep. Temperature can also be monitored and determined using a thermoresistor (thermistor) or alternatively two differing conductive fabrics and/or threads, to measure electrical resistance at varying temperatures.

Pressure sensors, such as functional textiles, can also be embedded in shelving units to monitor inventory levels when they are running low or when items are not being renewed over a period of time. A real-time inventory system using a SMART shelving system can communicate inventory levels and a software component could be built to automate the ordering process.

Figure 10:
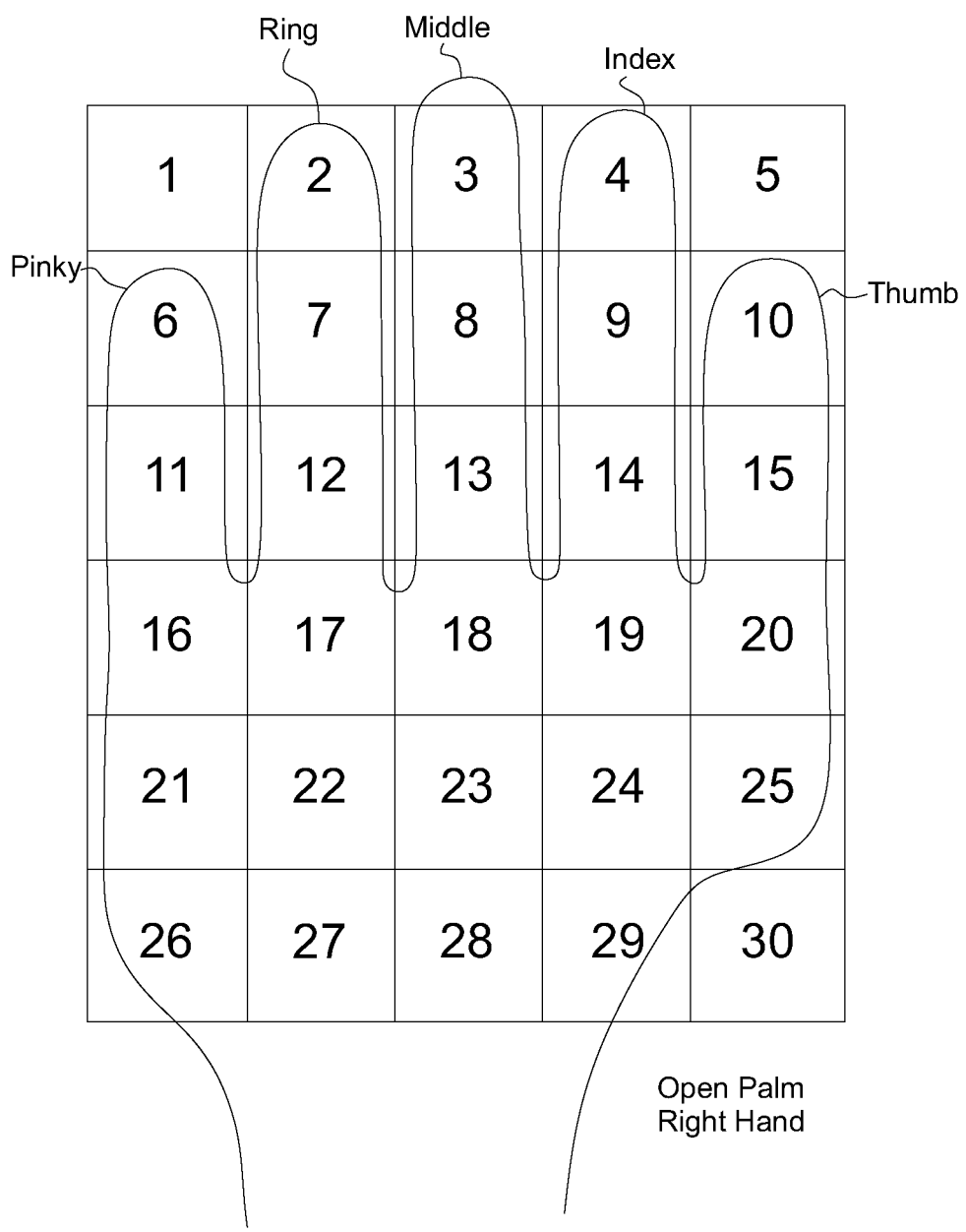
FIG. 10 shows an example embodiment of a flexible conductive apparatus system for artificial exterior skin allowing a robotic hand to have the sense of touch.

Yet another example application as shown in FIG. 10 is a flexible conductive apparatus system of an example embodiment in artificial exterior skin layers to provide the sense of touch to a robotic component such as a robotic hand. With the ability to determine amount of pressure with the sense of touch, a robot is configured to perform tasks that require further sensitivity such as being able to pick up delicate materials such as glass objects, without shattering it as a result of too much force applied. The robotic component may also comprise a stimulus feedback response mechanism, communicating with an external element such as a user, a person, a device, and/or system. This is also a beneficial component in settings where having haptic feedback is advantageous. For example, in remote control settings for improving the safety of controlling robotics in explosive ordinance disposal (EOD) situations that may require a degree of sensitivity in handling delicate objects and knowing how much pressure is being applied. Another example embodiment is for clinical settings where a robotic component may be controlled from remote regions by surgeons that have specific expertise in performing certain types of operations. Another example embodiment is in manufacturing that requires the sensitivity of touch to improve the efficiency of tasks on a production line.

The flexible conductive apparatus can be used by itself, or it can be integrated with other objects to create functional textile instruments.

Two Layer Flexible Conductive Apparatus

Another example embodiment of a pressure sensor is described, comprising two layers of conductive materials with same or different levels of conductivity, and a design/setup with increased points of contact at each intersection of the two layers as a method combining a capacitive method of sensing to determine location, and resistive method of sensing to determine variability of force or pressure applied based on the amount of points in contact corresponding proportionally with the amount of points coming into contact at the intersecting point. In one embodiment, the pressure sensor comprises a conductive fabric or textile sensor.

With the development of interactive and smart textiles by integrating metallic type fibers with textiles as one method, electrical circuitry has changed how materials operate with conducting electrical currents. Levels of conductivity differ among the many materials available, and which also adds to the varied levels of inherent air resistance and insulation, or resistance of the materials relative to the conductive components by weight.

Having this difference in levels of conductivity between the two layers of highly conductive material eliminates, in an example embodiment, the need for a middle layer of resistive material, since this difference effectively acts as a barrier to a complete circuit and functionally carries out the same purpose as a middle resistive layer. In turn, in an example embodiment, this elimination of the middle layer reduces production costs. Current passing from a material having a lower level of conductivity will never reach a level higher than its own capacitance, when in contact with a material having a higher level of conductivity. Differences in capacitance can be measured and monitored during application of pressure where the two materials come further into contact.

In an example embodiment, the sensor or apparatus can be supported by one or more rigid layers for each conductive path. Rigid means a non-compressible surface, or a surface that is sufficiently rigid and low elasticity so as to be perceived to be non-compressible, without bending or stretching of the sensor apparatus.

In one embodiment of a flexible conductive apparatus in accordance with an example embodiment for detecting force or pressure applied to said apparatus, the apparatus comprises a first conductive path having a first level of conductivity and a second conductive path having a second level of conductivity different from the first. The first and second conductive paths are positioned such that they are in contact with each other. The apparatus also comprises a plurality of sensor areas. Wherever the first conductive path contacts the second conductive path and is in electrical communication, each of these contact intersections gives rise to a sensor area which generates a signal corresponding to the applied force or pressure.

As used herein, a "conductive path" refers to an electrical conductive path. In example embodiments, the conductive paths are made from conductive fabrics or textiles arranged in a particular pattern. Alternatively, conductive threads can be used to create conductive paths; however conductive threads are not used in some example embodiments since they have limitations in maintaining voltage strength through the conductive path over a distance, (approximately exceeding 10 cm in length for some conductive threads). In some embodiments, the conductive paths are made from a combination of conductive fabrics and threads to overcome this limitation. Connecting a conductive fabric with a conductive thread acts as one conductive path with a larger surface area. In example embodiments, a conductive path is provided as a layer or supported on a layer, and placed in contact with a second such layer of conductive path, forming a flexible conductive apparatus in the form of a sensor sheet.

As used herein, "sensor areas" refers to intersections or areas of contact where a first conductive path is in electrical contact with a second conductive path to complete a circuit. Each sensor area generates a signal corresponding to the applied force or pressure.

The flexible conductive apparatus functions contrarily to conventional wires. Conductive components are blended with non-conductive components to create the conductive paths, which provides a level of surface area resistivity. The greater the surface area of each sensor area, the less the resistance the current experiences when passing from the first conductive path to the second conductive path. The resulting signal when the circuit completes is then processed to determine the amount of force/pressure applied.

Applied force or pressure resulting in one hundred percent contact between the conductive paths will create the maximum threshold for a complete circuit. On the other hand, due to natural surface area resistance of a conductive path, a less than one hundred percent electrical contact results in a complete circuit that is less than the maximum threshold. This is made possible by varying the levels of conductivity of the materials. Material specifications differ when conductive components are combined with non-conductive components thereby creating natural air resistance and insulation. In turn different materials require different amounts of force to be applied in order for a circuit to complete and reach its maximum threshold.

In one embodiment of the flexible conductive apparatus, a complete electrical contact between the first and second conductive path at any one of the plurality of sensor areas will generate a maximal signal. Where there is partial electrical contact between the first and second conductive path at any one of the plurality of sensor areas, this will generate a less than maximal signal.

Conductive Material

A minimum of two conductive paths are required to make contact and complete a circuit. Sensitivity of the flexible conductive apparatus of force or pressure can be adjusted by using different materials with different levels of resistivity to make a conductive path, which also results in different levels of surface area resistivity. Selection of a different material will yield a flexible conductive apparatus with a different level of sensitivity, and in turn a different conductivity and therefore different surface area resistivity. For example, using a material having a lower conductivity and higher surface area resistivity for one of the two conductive paths will decrease the level of sensitivity of the apparatus since there is greater resistance to completing a circuit. In an alternate embodiment where a conductive layer is provided between the two conductive paths, using a material having a lower conductivity and higher surface area resistivity than the two conductive paths, this will also decrease the level of sensitivity of the apparatus.

Conductive Path Design

In a two-dimensional plane, the design of a conductive path can be manipulated in patterns such that when the conductive path is provided as a layer or supported on a layer, there are conductive areas and non-conductive areas. For example, in some embodiments the conductive path runs linearly with gaps in between each linear segment. Turning to FIG. 1, in the illustrated embodiment, a vertical conductive path overlaps with a horizontal conductive path in a grid pattern. The resulting sensor areas, where the two conductive paths are in electrical contact, are arranged in a matrix. In other embodiments, repeating patterns and units can be used as shown in FIGS. 2A, 2B, 2C, 2D, 2E and 2F, or other variations or shapes separated by spaces of non-conductive areas. Other patterns and shapes such as squares, rectangles, diamonds, and circular designs can be customized to accommodate needs. In some embodiments, the circuit setup for the conductive paths includes a pair of multiplexers (MUX), where the power signal is input into one (MUX) and the output signal is read from another MUX. Single and multiple combination of multiplexers can also be used.

Turning to FIG. 2D, in one embodiment for a two-dimensional plane, the first conductive path has a repeating spiral design to halve the amount of material being used. In some embodiments, the second conductive path also has a pattern design. In an example embodiment, to maximize the surface area of each contact point or sensor area, the second conductive path is provided as a continuous sheet. In another example embodiment, the second conductive path has a repeating square design, wherein each square unit of the repeating square design of the second conductive path overlaps with a spiral unit of the repeating spiral design of the first conductive path. In this manner, the total surface area of all the sensor areas is determined by the surface area of the spiral conductive path. A maximal signal is generated when there is 100% contact at all the sensor areas (and along the entire surface area of the spiral conductive path). Accordingly, when pressure/force is applied and the two conductive paths contact to complete the circuit, the output signal value reading is proportionate to the total surface area of the sensor area that is in contact.

In a three-dimensional plane, curvature and/or contours of the conductive paths and sensor areas are determinants of variations in the output signal value which would be distinguishable in three-dimensional space. For example, in an application of the flexible conductive apparatus as an artificial exterior skin layer for a robotic hand, positioning can be differentiable between a finger pointing straight or a finger being curled. The curvature at the tip of a finger would read a signal value that is different, thereby differentiating a pointing finger over a finger being curled. Another example application is visualization of three-dimensional mapping based on the amount of force/pressure applied on the sensor areas. As each sensor area can differentiate amount of force/pressure applied, a three-dimensional image can be outlined to demonstrate that an artificial exterior skin layer can determine where on a robotic hand an object exists in one example, and how heavy that object may be.

In accordance with general electrical circuitry, the flow of electrical charge has voltage that travels at a relatively quick speed as compared to the speed of light. Manipulation of design and the path of travel can alter the outcome of the speed of travel of electricity in a single circuit and create a delay in the path and slow down the speed of travel of electricity that is noticeable to the human eye. An example of the manipulation of design to alter the outcome of the speed of travel of electricity is that if a setup with only one point of contact for a sensor area 112 at which a connection would need to exist for electricity to travel to its destination, the speed of travel would be relatively fast as compared to the speed of light. Through manipulation of the design, an example requiring three points of contact 306 to make connection, a completed circuit with the electrical output signal will depend on the number of points being in contact. (See FIG. 3)

To further add to the manipulation in the time it takes for an electrical charge to reach its destination in a completed circuit, materials with varying levels of conductivity can also impact the speed of travel.

Sensor Areas

Each sensor area is unique at each intersecting or contact point. The signal generated by each sensor area can be manipulated by the applied force or pressure applied. By way of analogy, the location of an applied force or pressure on a weight scale will influence the weight reading. For example, standing on the edge of a weight scale will output a value different than standing in the center area of the weight scale. Increasing the surface area of each sensor area along with modifying the designs of the conductive paths will change the output value of the signal when a circuit completes (see Table 1 below). With the increased surface area of each sensor area acting similar to that of a weight scale, movement is detected by monitoring for variations in the output signals due to redistribution of applied pressure/force or contact over the sensor area. In contrast a stationary object will output a consistent signal value.

Hardware and Data Systems

In one example embodiment of a system, a flexible conductive apparatus 702 is attached to a hardware unit 704. The hardware unit has a receiver for receiving a signal from each sensor area, and a processor for processing the signals into pressure data. The pressure data is then stored and analyzed in a database network 706 and 708 each comprising one or more databases. An example system is illustrated in FIG. 7.

In some embodiments, the flexible conductive apparatus is connected to a hardware unit comprising components including a microcontroller, a single board computer that comprises of a wireless and wired network capabilities, a processor, multiplexers, analog-digital converters, amplifiers, alerting device, speakers, buzzers, LEDs/LED strips, accelerometer, gyroscope, or combinations thereof. The signals are read through a microcontroller and microprocessors and the signals are optionally amplified with amplifiers, resistors, and op amps that are converted to digital signals. The signals are optionally passed through a band-pass filter, filtering high frequency and low frequency signals.

In an example embodiment, the system has sensory feedback system. For example, the system may have lights and sound that is embedded for user interaction and communication of information (See FIG. 7). An example of such a sensory feedback system for user interaction may be an outcome 710 by way of example as an alarm that could be set in the event of a health related incident such as a fall, or a heart attack, or a stroke. Another example of an alternative outcome 712 may be for a baby that experiences apnea after X number of seconds of no movement, the device can activate an alarm. Outcomes may be customized to fit suitable applications as needed.

Sensory feedback is customizable to accommodate different conditions and the needs of the user receiving the feedback. The hardware unit may also optionally comprise of LED lights and speakers which could be activated to indicate and/or communicate different conditions of respiration, posture, location and movements. For example, breathing within a normal range can indicate a neutral color such as green, whereas a higher or lower than normal respiration rate can be orange or red to signal caution.

Figure 11:
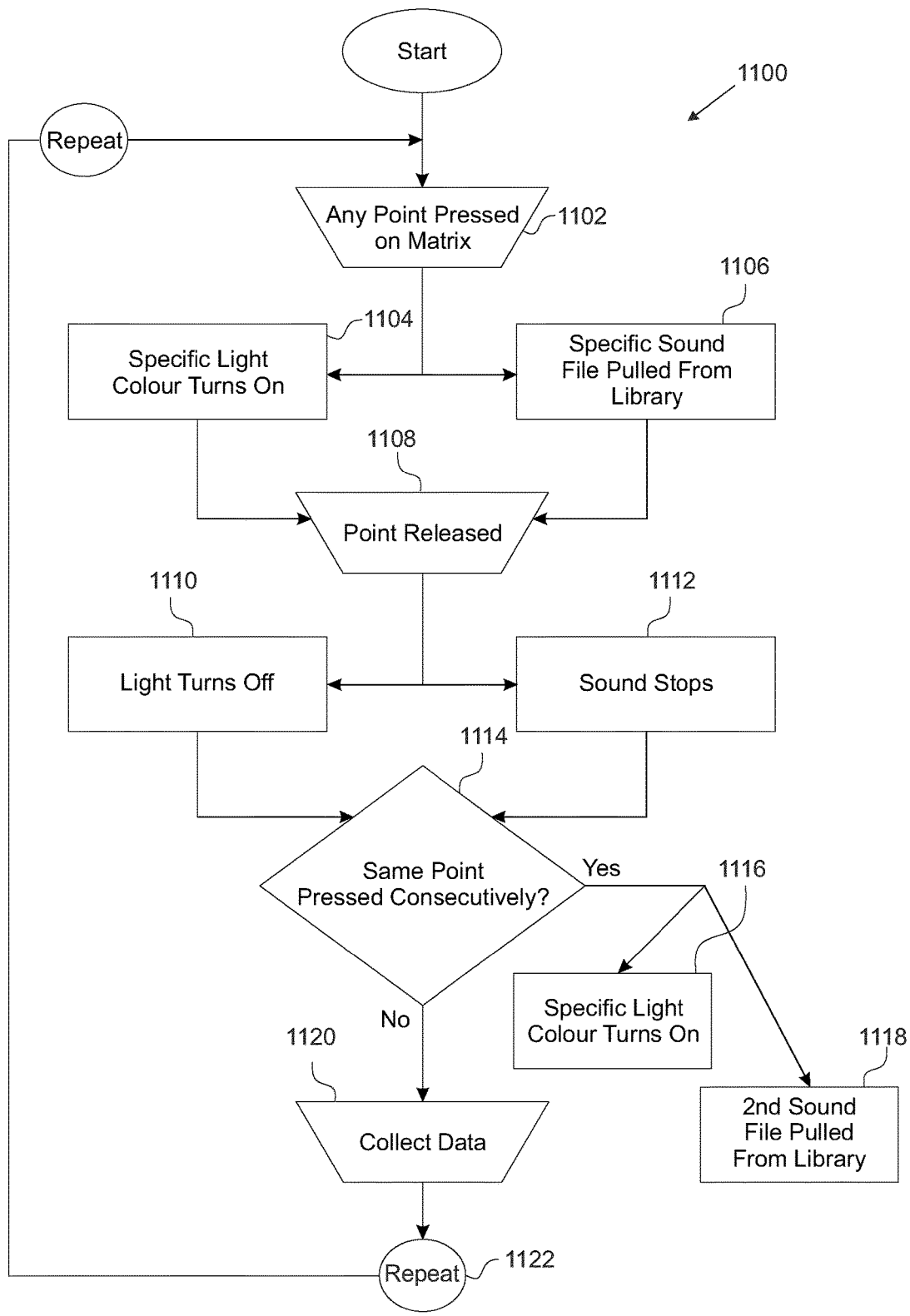
FIG. 11 shows a flow chart for an example sensory feedback system.

FIG. 11 illustrates an example flowchart 1100 of a method for a sensory feedback system with lights and sound using the flexible conductive apparatus 702 and system 700. As each sensor is unique and can measure variability of pressure applied, feedback through output devices that may include lights and/or sound can be set to have outcomes based on user interaction.

At event 1102, it is determined that any point is pressed on the matrix of the flexible conductive apparatus 702. An indicator is then output to an output device to signal to the user, for example event 1104 to turn specific light color on, and/or event 1106 to retrieve a specific sound file from library and output to a speaker. At event, it is determined that the point pressed on the matrix of the flexible conductive apparatus 702 is released. The corresponding light is turned off (event 1110) and/or the corresponding sound stops (event 1112). At event 1114, it is determined whether a same point on the matrix of the flexible conductive apparatus 702 is being pressed consecutively. If yes, then at event 1116 specific light colors turn on (can be different than the specific lights at event 1104) and/or at event 1118 a second sound file is pulled from the library and output to the speaker. If no, at event 1120 data is collected, and stored and/or sent to the database network 706, 708. At event 1122, the flowchart 1100 loops by repeating to event 1102.

In some embodiments, referring again to FIG. 7, the collection and transmission of pressure data to a data network is accomplished by a wired or wireless connection from the hardware unit 704 to the database network 706, 708. Wired or wireless networks can be more than one type of wireless networks (e.g., LAN, WLAN, radios, Bluetooth). Input values are classified by a timestamp, and the location (X, Y, and/or Z coordinates) by the receiver at each individual sensor area. For example, when contact input is generated at a sensor area, the varying value of that sensor is recorded as well as the time, location, and amount of force/pressure that was applied. In addition, user inputted data such as user information may be saved with the sensor information of the user (e.g., user's age and demographic information) to a database of the database network 706, 708. Data is stored into a database and can be hosted either locally or optionally also to a cloud server. Data from the database is used for multiple purposes, including for example: 1) Notification system for the detection of a set time duration of no change or change exceeding a set threshold of values that a sensor records, 2) Real-time feedback applications, and 3) Analysis of data from contact input for predictive models. All processed data are then stored into new databases and all databases are encrypted.

Raw inputs from the functional textile instrument can be grouped before entering the database to provide a faster collection of inputs. All incoming raw inputs can be set to specified ranges and the indicating pressure in terms of values (increasing or decreasing values) can be predetermined.

Raw data of electrical signals can be processed on the hardware unit 704 for Digital Signal Processing before data is stored to the database network 706, 708. This includes any error correction, to flag outliers, and using statistical calculations for signal processing.

In an example embodiment, error detection and outlier detection may be implemented. Error detection is determined if the incoming value per sensor is unchanged over time or if the values stay within a specified percentage of the total maximum value. Errors are determined if values fall outside a specified range of value and any irregular characters such as alpha and special characters that are created due to sampling from the microcontroller. For example, if the incoming values are set from 0 to 1024 and the incoming values occurs outside 0 or 1024, or wavers between 0-5 (approximately 0.5% of 1024), this is considered an error in the sensor in one example. The locations of the sensors are calibrated, thus, any errors in the sensors can indicate which location of the mat is disabled.

Outliers are determined by using techniques such as moving window, examining residuals to determine if values are greater than a specified interquartile range, or examining values greater than a specified threshold such as a specific standard deviation or using Fourier transforms and spectral density calculations.

Calibration and normalization can also be performed. Calibration is gathered within an initial time window (e.g., first 30 seconds) when no object or person is on the sensors by reading the raw signals. Using the raw signals collected for each sensor, a calibration technique is executed. One technique is to gather the maximum value, the minimum value, mean, standard errors to calculate a standardized score, and standardized residuals for each sensor. One technique for normalization is to calculate the maximum value, minimum value for each sensor during the time window and subtract the minimum value from each value and divide it by the range of the values within the time window. This will turn each sensor value between the range of 0 and 1.

Classification of Movement and No Movement

Returning to FIG. 6A, presence or absence of movement is determined using the electrical signals collected from the flexible conductive apparatus 702. This example embodiment will illustrate detection of movement and no movement of a living being using the flexible conductive apparatus 702.

Step (1) A detection of "contact" versus "no contact". For example, one technique is based on a calculation of meeting an absolute threshold across all sensor areas and meeting a difference threshold that examine a change in values for each sensor area. The first few hundreds of values are calculated to give an initial mean, median, and an initial variation threshold. After, the past (x−1) and current values (x) are always compared for each sensor area. For each sensor area, rolling means and rolling standard deviations are taken for every interval of a specified amount of seconds. If the value is less than a predetermined mean threshold (e.g., <100), it is considered "no contact". If the incoming value is greater than the difference threshold for that sensor and the value is greater than the mean threshold, then the value is considered "contact". Transformations and baseline calibrations (e.g., subtracting the variations of the first hundreds of values when there is no contact) may also be applied to all incoming signals to reduce the "noise" of incoming signals. Other techniques include Fourier Transforms and Power Spectral Density which are also performed for all sensors signals, breaking down the signals into sinusoids functions. The sinusoid function for each sensor is then compared relative to the other corresponding sensors. The ones with the largest or most peak amplitudes in specified frequencies will also indicate when there is contact. An average of all Fourier Transforms for each sensor is integrated to produce one signal per point in time. Transformations to the signals allows amplification of the signals to provide better distinctions of the signals.

Step (2) All the "contact" sensor areas per given time is categorized and divided into multiple regions. A concentrated region, for example, includes the torso area where breathing movement is captured or the region that provides stronger indicating output signals. After examining the mean and the variation of each sensor area over time, sensor areas with the lowest mean, median, and residuals as well as the least variation is determined. Sensor areas with the greatest mean and the most variation are also determined. Area about these identified sensors may additionally be mapped onto a graphical representation, for example a heat map to determine the locations of interest. The greatest variation is considered to be characterization of movement and the least variation is considered to be closer to no movement. In addition, specific frequencies can be specified for respiration and other vital signs such as heart rate with calculations using Fourier Transforms, power spectral density calculations, correlation methods, autoregressive models, power spectral density, and cluster analysis which can determine regions of interest.

Step (3) A target area is highlighted to monitor movement. Importantly, a detection of movement is determined in comparison to readings where there is no movement. The mean and variation is calculated for movement vs. no movement. When there is no movement, the variation threshold is smaller than when there is movement. Optionally, the target area is also mapped by sensor locations and the use of regression models and machine learning models to determine the breathing activity. Frequency for respiration and movements are also different and can be specified to give insights on movements as well.

Timer/Alarm System

In some example embodiments, the system may additionally comprise a timer system for initiating a visual or auditory notification based on a predetermined set of parameters. For example, a timer and alarm system, where an alarm is sounded after a detection of a specified number of seconds of no movement. For detecting an absence of movement, several procedures are considered. Or in another example, an alarm is sounded after a detection of signals above or below a set range of parameters, equating to a determined amount of force/pressure applied. For example, in a compression instrument where a set amount of pressure must be maintained to stop traumatic bleeding, muscular tendencies may constrict over time and an alarm can sound to notify if retightening of the compressing instrument is needed to prevent venous and/or arterial bleeding. A timer may also sound if the compressing instrument had been applied for a prolonged period of time to notify and prevent risk of permanent damage.

When all sensor areas corresponding to the target area display no movement, that is, with minimal variation of the values over a specified predetermined interval, an auditory and/or visual alarm may sound. The minimal variation over the specified interval across sensor areas in the target area will send a signal to the hardware device and triggers an auditory sound and/or a visual alarm on the monitor of an application. This checking of minimal variation is done for each iteration. A timer is set at a specified amount of seconds for each iteration.

Device Compatibility

The system is compatible for the use in both browser and mobile devices. A real time monitoring application interface may provide information and graphical representations about the user, the conditions, timer, the alarm, the breathing rate, the breathing analysis, pressure applied, lack of required pressure, or any such variation that can detect variation through contact input. The interface also allows users to input user information which will be linked to the sensor information output from the hardware. This real-time monitoring application interface will be retrieving information from the database network.

Detection of Object versus Humans

Means, variations, frequencies of signals are determined over time whether there is a significant change. If values of the "contact" sensors show no change or minimal variation over time and if the raw input values are within a small range, then this triggers the possibility of a still object.

The following examples are further illustrative of various aspects of example embodiments.

The flexible conductive apparatus 702 can be made using various combinations of materials with different combinations of conductive properties depending on the desired level of sensitivity from the hardware component alone.

A 5 volt power source is attached to the flexible conductive apparatus 702, recording output values in a range in one example, from 0-1024 based on measuring the maximum threshold values from a completed circuit with the same amount of force/pressure applied. Different materials will output a different maximum threshold based on the amount of force/pressure, where a high conductive material will reach a maximum threshold that is higher than materials with lower levels of conductivity (see Table 1 below). As threshold values differ by using different material combinations and amount of force/pressure applied, sensitivity can also be adjusted by using the improved 2 layer system rather than the 3 layer system.

As thresholds will not reach a maximum value (e.g. 1024) based on 5V input due to natural resistive elements of current carrying conductors, order and combinations of materials may create time differences for completion of a circuit.

TABLE 1

| Material Testing: output value range from 0-1024, 5 V power source. | | |
|---|---|---|
| Material List: | | |
| O= | Original Material, Conductive Fabric, 1 sided | |
| M= | Resistive Mesh Layer | |
| V= | Resistive Plastic Type Layer | |
| G= | Green Conductive Fabric, 2 sided | |
| S= | Silver Conductive Fabric, 1 sided | |
| | Range From: | Maximum Threshold |
| Combination: 3 Layer | | |
| O - G - O | 230 | 825 |
| O - V - O | 40 | 823 |
| O - M - O | 8 | 800 |
| S - G - S | 80 | 640 |
| S - V - S | 3 | 370 |
| S - M - S | — | 440 |
| G - V - G | 35 | 520 |
| G - M - G | 4 | 410 |
| Combination: 2 Layer | | |
| O - O | — | 823 |
| O - G | 300 | 710 |
| S - O | 350 | 680 |
| S - S | 33 | 283 |
| S - G | — | 410 |
| G - G | 292 | 463 |

Conductive Path Designs

Example Design 1: an example of a flexible conductive apparatus setup for a system to detect pressure for a flat, non-compressible surface is a two-layer design with the conductive textile that combines conductive and non-conductive threads that are "weaved/knitted" in a grid-like pattern where non-conductive threads provide separation from the conductive threads, where a first conductive path 302 is set up to run in one direction and a second conductive path is set up to run in an intersecting direction 304, thereby when the two conductive paths are overlaid, a grid pattern results with each intersecting point forming a sensor area 112 that can measure variability based on a first level of resistance of non-conductive threads separating the first and second layers, and the second level of resistance from the non-conductive threads separating the conductive threads on the same layer. As there is separation from the conductive threads, applied pressure from external forces will compress the two layers making contact of the intersecting conductive paths at different points 306 allowing variability of electrical signals to be measured correlating to the amount of pressure applied.

Example Design 2: an example embodiment of a flexible conductive apparatus setup for a system to detect pressure for a surface with changing form factors by way of example as a bed, is a three-layer design with first and second conductive paths 504 and 508 separated by a middle layer 506. The middle layer provides resistance through dispersion from the first and second conductive paths 504 and 508 coming fully into contact for situations such as if portions of the flexible conductive apparatus is bunched closely.

Example Design 3: A third example is where one layer has a spiral design 204 that creates gaps for lower surface area conductivity. The opposing layer 200 would have higher surface area conductivity to eliminate gaps so that variation could be determined from points coming into contact. If the example described were flipped, a small point of contact made at an area where there is a gap may not read an output value similar to the previously demonstrated example.

Example Design 4: A fourth example includes an efficient method for using less materials by combining conductive fabric and thread: an example being a 1.27 cm (0.5 inch) conductive fabric 212 and a conductive thread 214 that are connected in a pattern that would increase the surface area equivalent to a 2.54 cm (1.0 inch) conductive fabric, but using less material (e.g., see FIGS. 2E and 2F).

Figure 12:
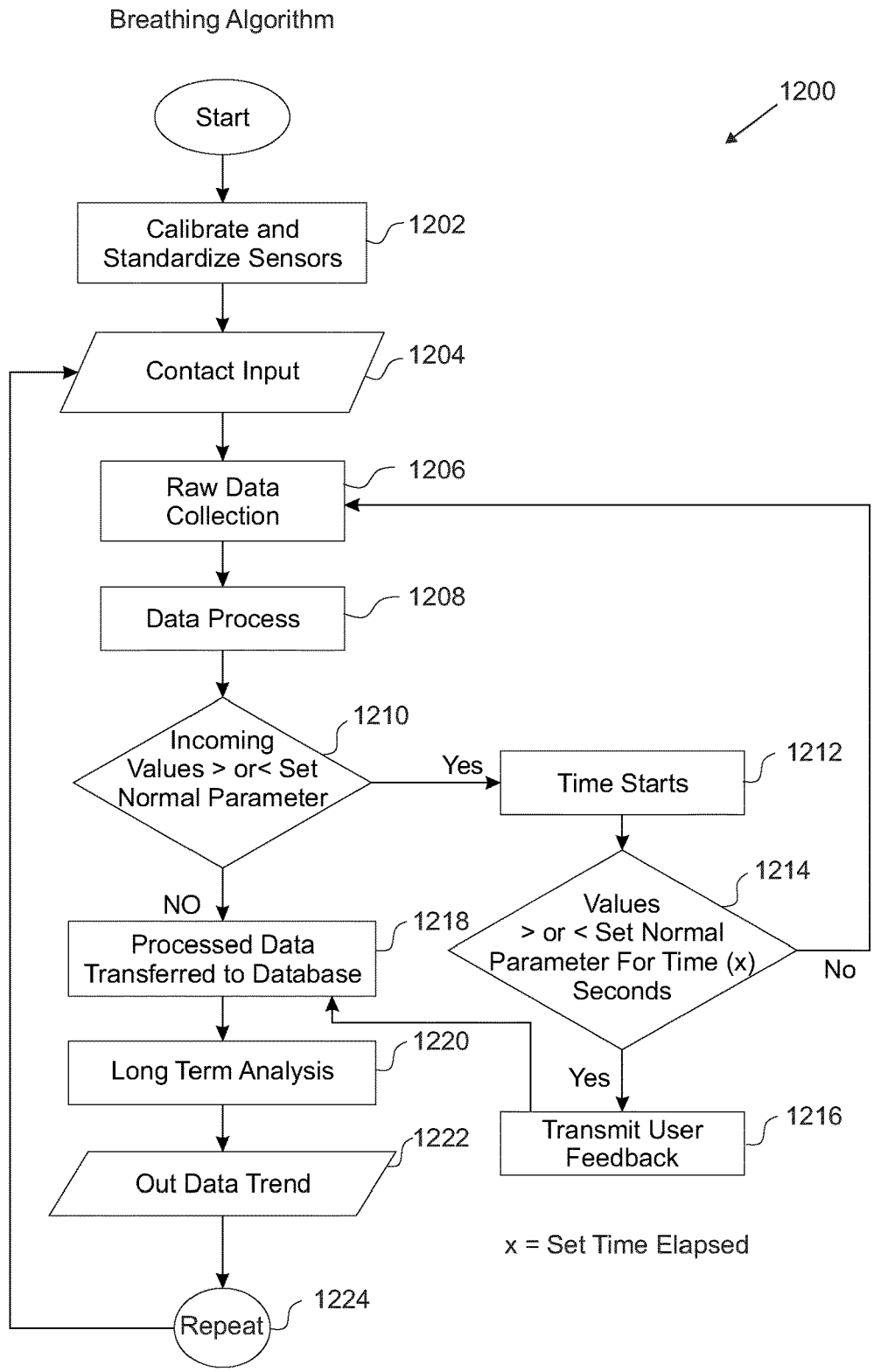
FIG. 12 shows a flow chart for an example breathing monitoring algorithm.

FIG. 12 illustrates a flowchart 1200 of an algorithm for breathing analysis and detecting conditions outside of normal set parameters, using the flexible conductive apparatus 702 and system 700 in an example embodiment. The torso is highlighted (see FIG. 6C) as a target area to monitor breathing activity in comparison to readings where there is no breathing. After errors and outliers are determined and excluded from analysis of breathing, torso regional areas are determined. Variations are calculated for breathing versus no breathing. Fourier Transforms are also conducted for each signal for all sensor points in an example embodiment.

At event 1202, the sensors of each of the flexible conductive apparatus 702 are calibrated and standardized. For example, a baseline signal can be determined when no object or external pressure is present on the flexible conductive apparatus 702. At event 1204, there is contact input detected one or more of the sensors of the flexible conductive apparatus 702. At event 1206, raw data is collected from the sensors of the flexible conductive apparatus 702. At event 1208, the raw data is processed. At event 1210, it is determined whether incoming values are greater or less than a set normal parameter. If yes, then at event 1212 a time starts. Further, at event 1214 it is determined whether the values are greater or less than the set normal parameter for a specified period, e.g. number of seconds. If not, the method loops to event 1206. Referring again to event 1214, if yes then at event 1216 there is transmitted user feedback to an output device such as a speaker, light or visual display, and then data proceeds to event 1218. All events are captured into the database network 706, 708, in an example embodiment.

Referring again to event 1210, if no then at event 1218 the processed data is transferred to a database network 706, 708. At event 1220, there is performed long-term analysis that can be based on the present patient subject, historical information, other patients, big data, etc. at event 1222, long term data trend is output. In an example embodiment, Long Term Analysis data may also be captured in the database network 706, 708. At event 1224, the flowchart 1200 loops by repeating to event 1204.

Figure 13:
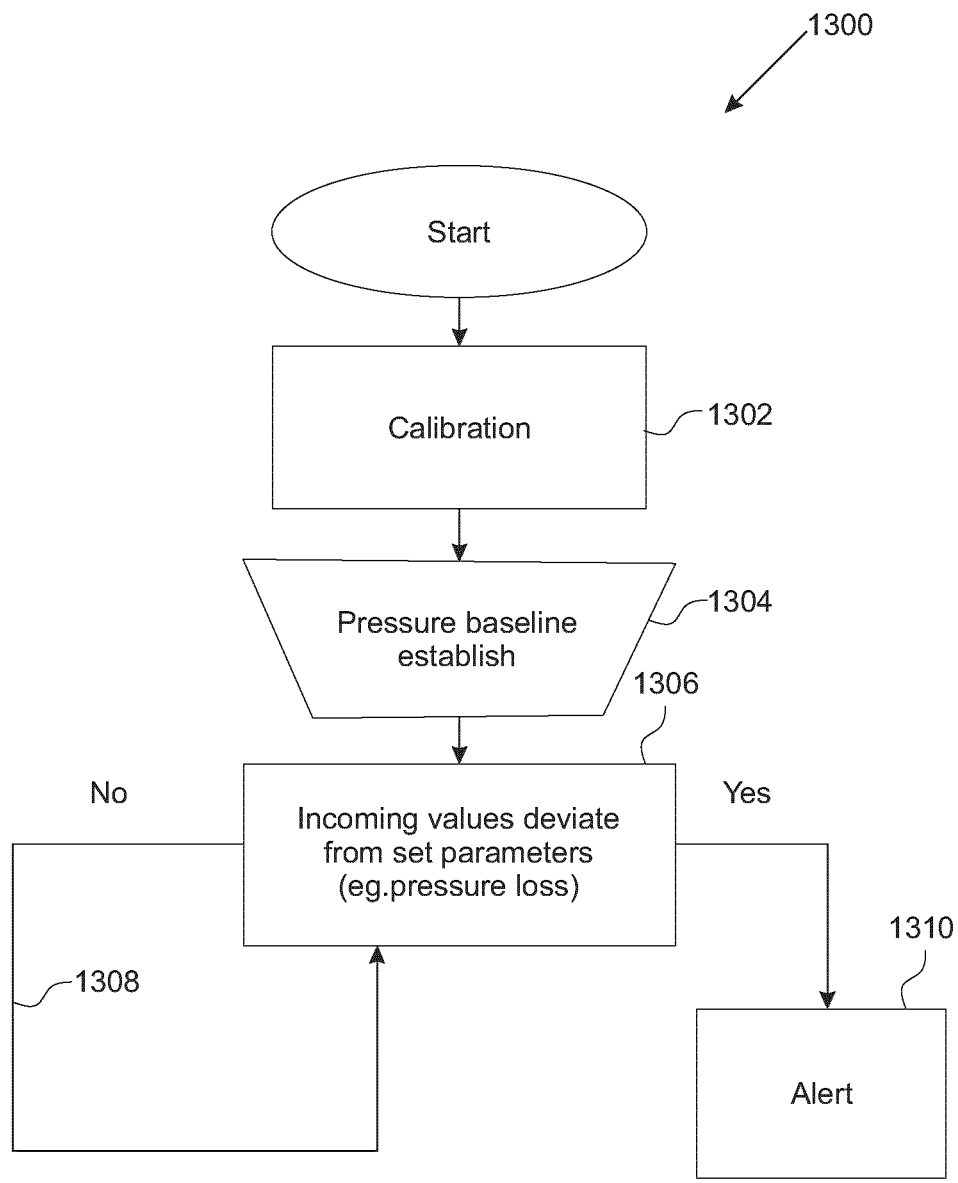
FIG. 13 shows a flow chart for an example system of monitoring pressure loss.

FIG. 13 illustrates a flowchart 1300 of an algorithm for monitoring of pressure using the flexible conductive apparatus system 700 attached to a combat application tourniquet. At event 1302, the system 700 once activated is configured to calibrate to the according pressure level as set by the applicator or through an automated setting of establishing a baseline for the pressure applied at event 1304. At event 1306, it is determined whether incoming values deviate from set parameters, e.g. pressure loss. If so, at event 1310 the system 700 can be configured to alert through an output device if there is a loss in pressure of the tourniquet until correct pressure levels are achieved again. If not, then at event 1308 the flowchart 1300 loops by repeating event 1306.

Figure 14A:
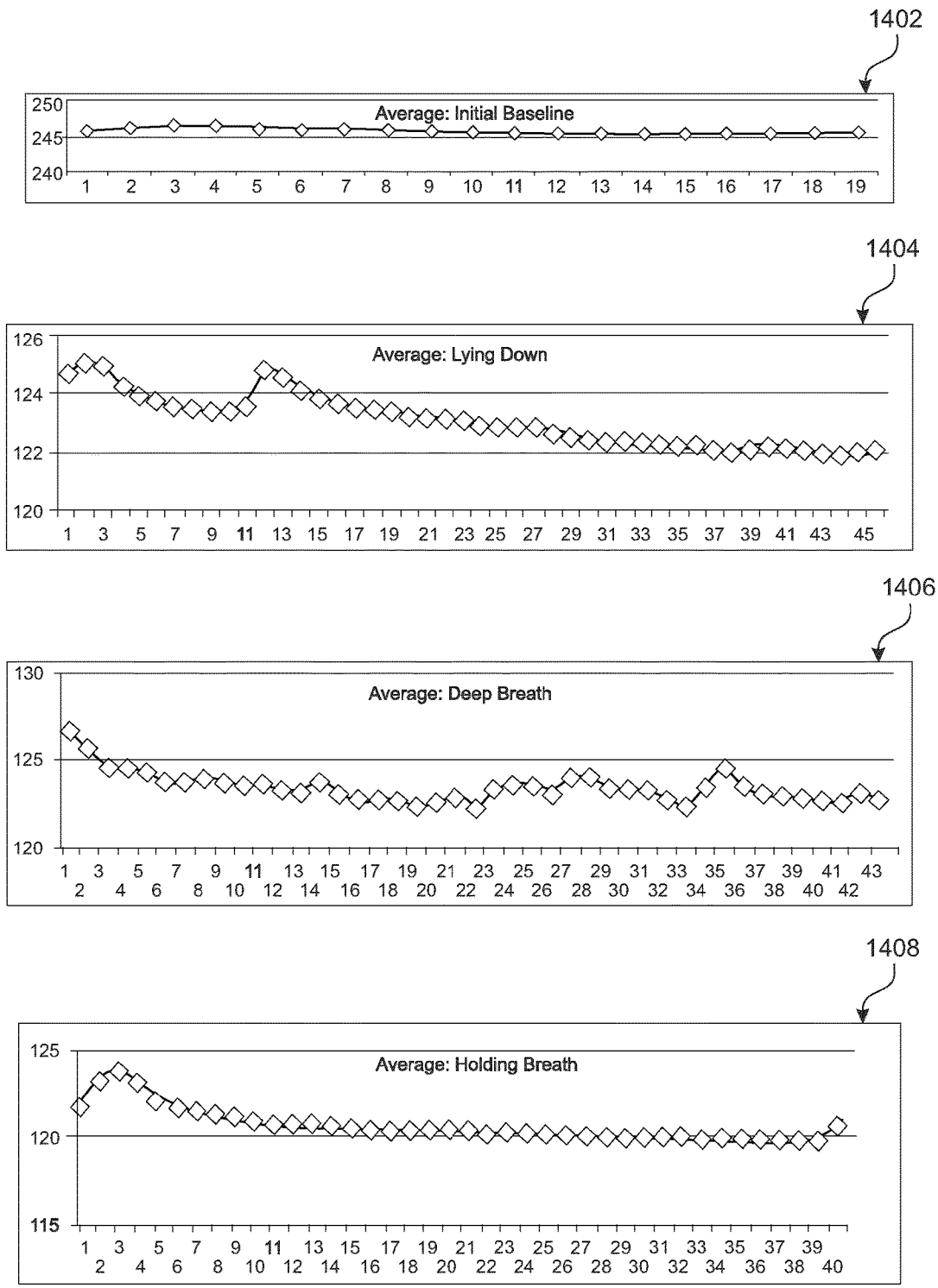
FIGS. 14A, 14B and 14C shows experimental results for monitoring breathing patterns using an example embodiment of a flexible conductive apparatus on humans.

Results of breathing analysis from an experimental controlled setting are shown in FIG. 14A. The graphs 1402, 1404, 1406, 1408 depict a mean average across all data across all sensors versus a time interval value. Illustrated is a graph 1402 that depicts a relatively stable signal when there is no object on the flexible conductive apparatus with averaged initial baseline readings. Illustrated is a graph 1404 that depicts a change in variation when there is a person lying on the mat when they are breathing without effort. Illustrated is a graph 1406 that depicts a change in variation from a person inducing deep breathing. Illustrated is a graph 1408 that depicts when a person is lying on the mat from normal breathing to holding their breath. Graphs 1404, 1406 and 1408 represent average of detected values subtracted from baseline value from graph 1402.

Figure 14B:
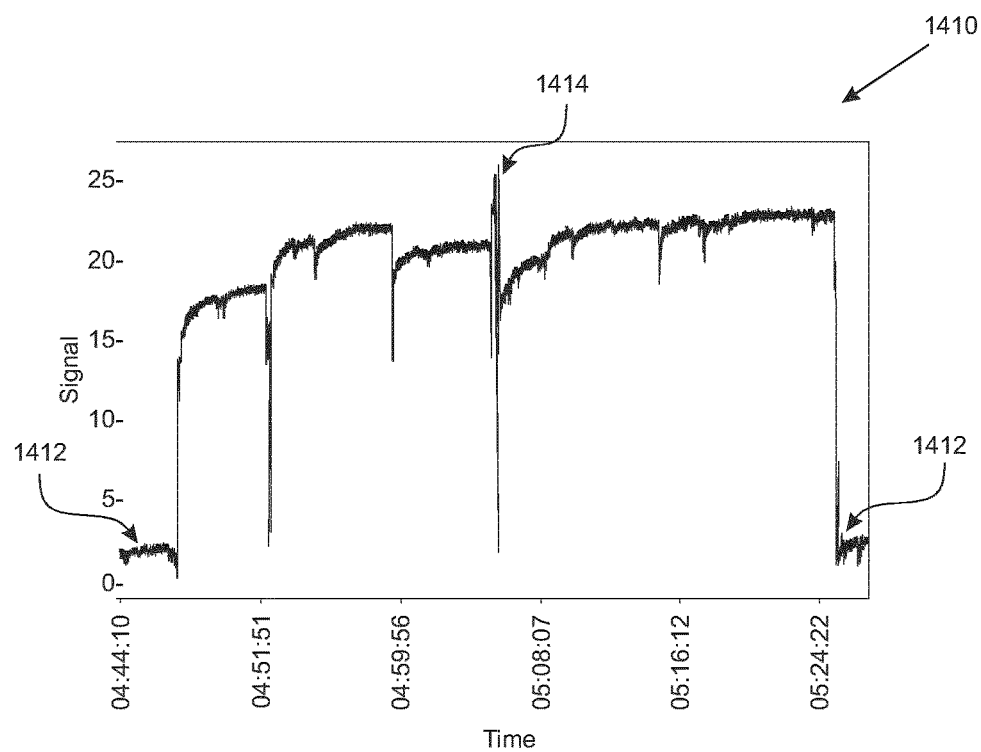
Figure 14C:
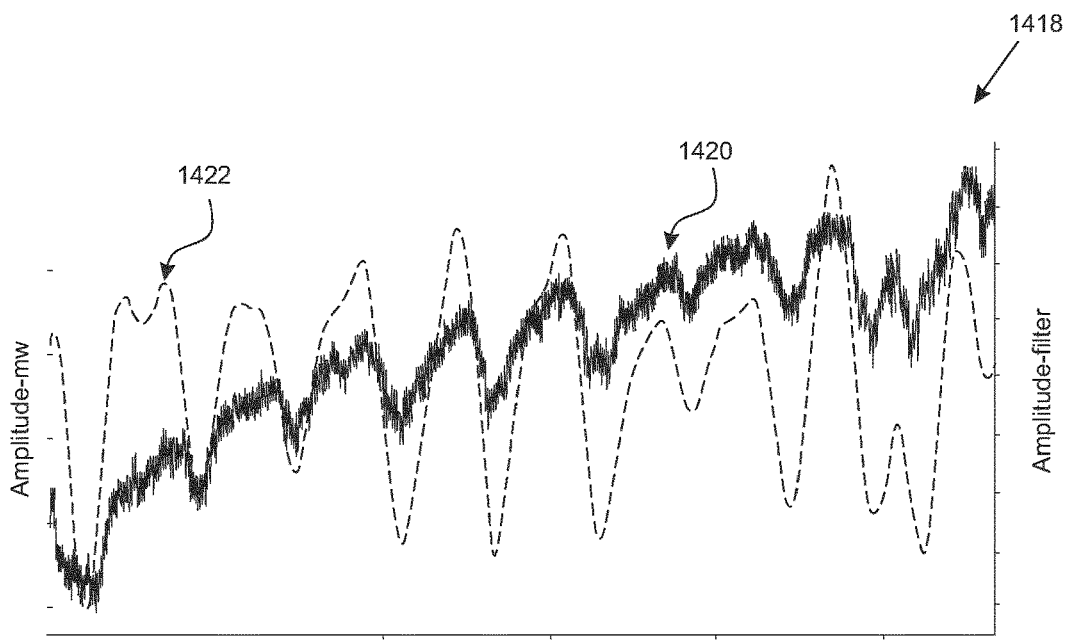

FIGS. 14B and 14C illustrate further results of electrical signals derived from experimental controlled settings that are translated into activity monitoring graph 1410 and respiration graph 1418. Illustrated in FIG. 14B is a monitoring graph 1410 that depicts activity prior to and following when there is an object on the flexible conductive apparatus indicated by signal 1412, and a spike in the signal 1414 indicating sudden movement resulting from a sneeze. Coughs may be determined by example through spikes in the signal that are greater than normalized settings, and less than the large spike 1414 resulting from a sneeze, occurring with higher frequency. Illustrated in FIG. 14C is a graph 1418 that depicts the respiration pattern of the person in the same experimental controlled setting of results from FIG. 14B. The raw signals are shown on the line graph 1420, with filtered and processed signals being shown on line graph 1422.

There is a significant difference between the variations such as the variation of deep breathing graph 1406 is greater than normal breathing graph 1404 and is greater than baseline graph 1402 or holding breath graph 1408.

Figure 15A:
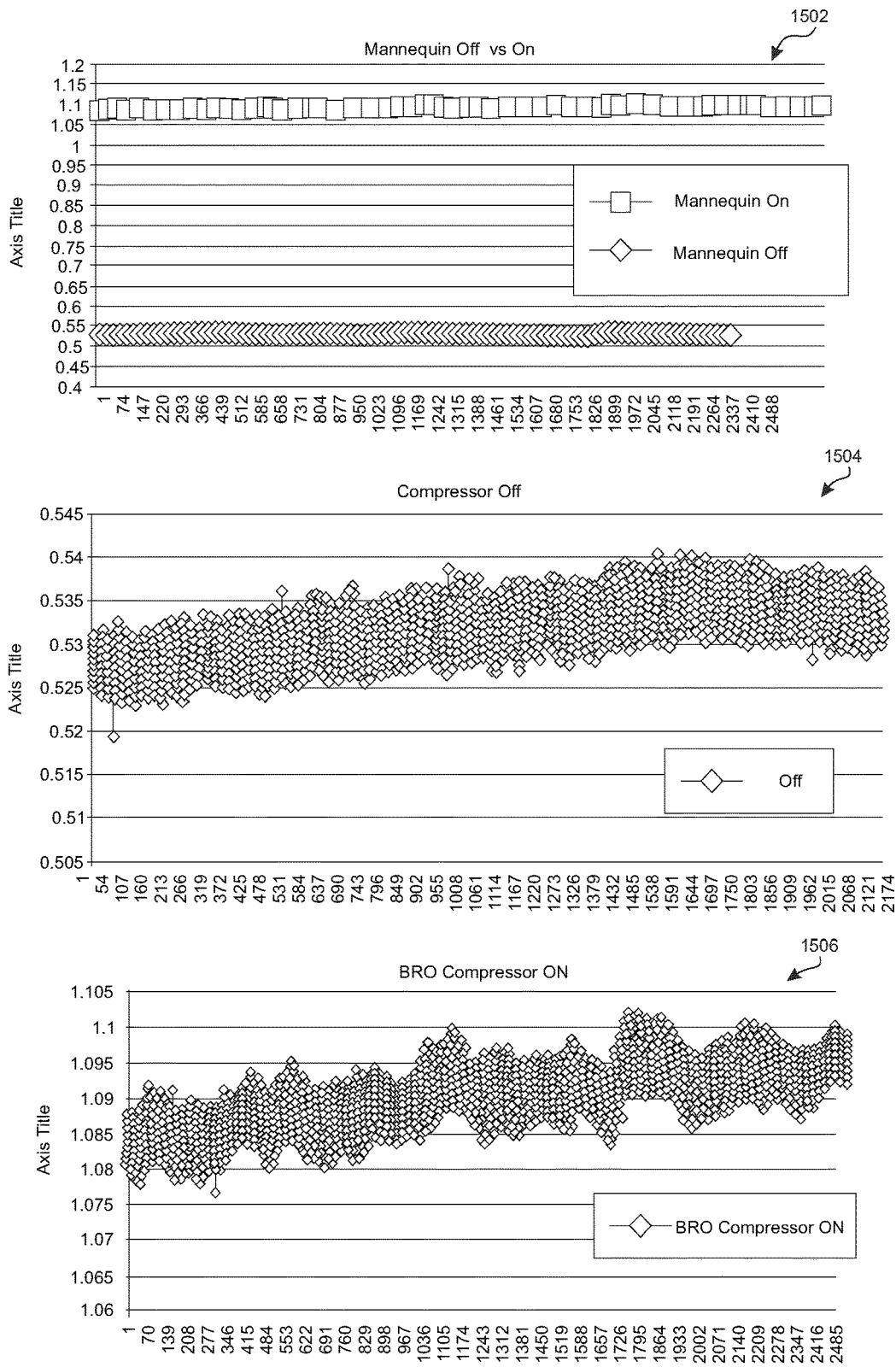
FIGS. 15A and 15B shows another set of experimental results in a clinically controlled setting for monitoring breathing patterns using an example embodiment of a flexible conductive apparatus using high technology mannequins.
Figure 15B:
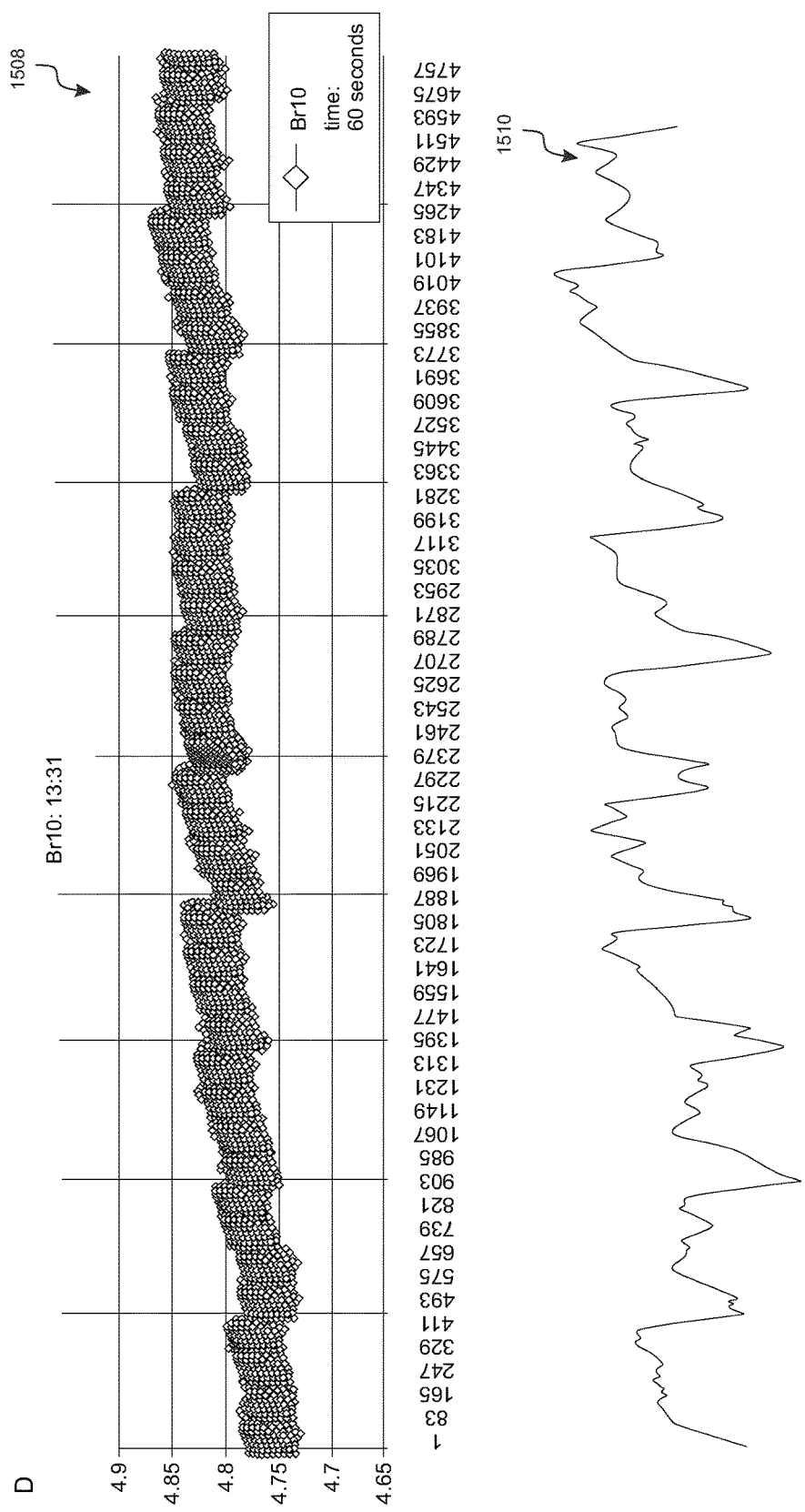

FIGS. 15A and 15B shows another set of experimental results in a clinically controlled setting for monitoring breathing patterns using an example embodiment of a flexible conductive apparatus, illustrating readings or signal values over time. Breathing patterns were simulated using a high technology mannequin with artificial lungs that are inflated by an air compressor, at breath rate zero ("BR0"). Comparison of baseline readings when there was no object versus when there was a mannequin placed on the flexible conductive apparatus is illustrated in graph 1502. Baseline readings of when the air compressor is turned off is illustrated in graph 1504. Baseline readings of when the air compressor is turned on but all vital signs are set to 0 are illustrated in graph 1506 while showing detection of slight vibrations from the air compressor that controls the high technology mannequin. The motor of the air compressor was located on the floor a distance away from the sensors, illustrating the sensitivity of flexible conductive apparatus.

Turning to FIG. 15B is a graph 1508 of another set of experimental results using a mannequin with artificial lungs to simulate breathing, breath rate ten ("BR10"). The volume of air inside the artificial lungs are controlled using an air compressor, which inflates and deflates the artificial lungs to simulate breathing. Illustrated are results from when the air compressor is turned on and simulated breathing is set to 10 breaths per minute in the graph 1508. Illustrated are additional results from when the air compressor is turned on and simulated breathing is set to 10 breaths per minute in signal 1510.

Figure 16A:
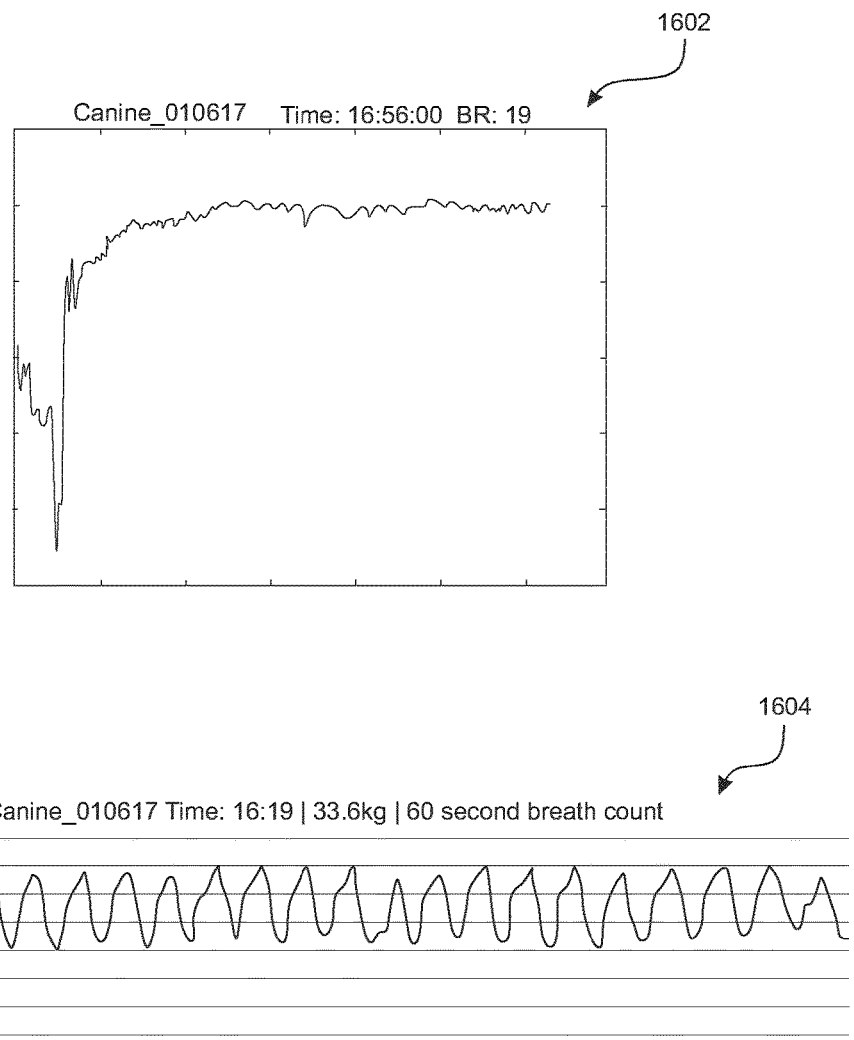
FIGS. 16A and 16B shows another set of experimental results of a controlled test of vital signs for a canine diagnosed with lymphoma.
Figure 16B:
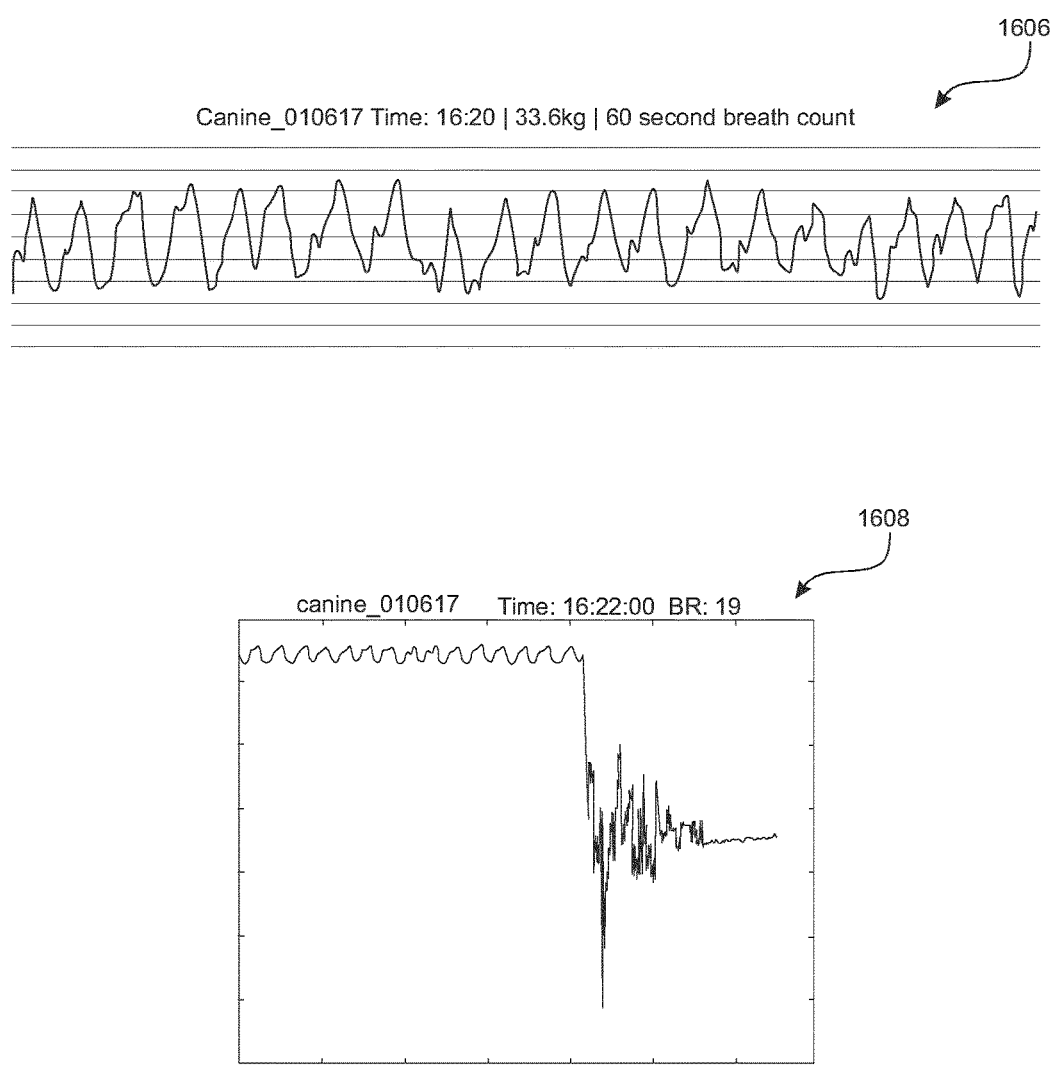

FIG. 16A shows a controlled test of vital signs for a canine diagnosed with lymphoma, at breath rate nineteen ("BR: 19"). Illustrated is a graph 1602 of signal values over time that depicts activity of the canine in the graph 1602 under controlled conditions from initially setting down on the flexible conductive apparatus in one embodiment, where the said apparatus determines the initial change from no object being detected to presence of an object being detected, then begins showing physiological signals after the canine lays down on the said apparatus. Illustrated is a graph 1604 of signal values over time showing the same canine with occasional respiratory difficulties with a recorded manual count of breaths for the first 60 seconds with relatively stable respiration patterns. FIG. 16B shows the same canine following 60 seconds showing irregular respiration patterns in graph 1606 including segments with multiple attempts of inhalation for a full cycle of breath at changing intervals. Breath rate is 22 ("BR: 22"). Illustrated further is a graph that depicts activity of the canine in graph 1608 under controlled conditions leading up to, and getting up and off the flexible conductive apparatus.

Similar analysis and/or methods can be applied to monitoring and detecting heart rate and temperature, in example embodiments.

An example embodiment is variable conductive apparatus responsive to applied external force, comprising: a first conductive path that includes a first conductive surface; a second conductive path that includes a second conductive surface, a part of the second conductive surface having a conductive contact surface area with a part of the first conductive surface when there is no applied external force, another part of the second conductive surface separate from another part of the first conductive surface when there is no applied external force, wherein the applied external force increases the conductive contact surface area between the first conductive surface and the second conductive surface resulting in an increase in conductivity between the first conductive surface and the second conductive surface.

In an example embodiment of any of the above described variable conductive apparatus, wherein the first conductive path is for receiving power from a power supply, and the second conductive path results in a detectable signal in dependence of the conductivity.

In an example embodiment of any of the above described variable conductive apparatus, wherein the received power is a DC voltage.

In an example embodiment of any of the above described variable conductive apparatus, wherein the detectable signal is less than a maximum signal defined by the power supply when there is no applied external force.

In an example embodiment of any of the above described variable conductive apparatus, wherein the detectable signal increases in correlation to the applied external force due to the increase in the conductivity.

In an example embodiment of any of the above described variable conductive apparatus, wherein the detectable signal is a maximum signal defined by the power supply when there is applied external force that maximizes the conductive contact surface area, resulting in maximized conductivity.

In an example embodiment of any of the above described variable conductive apparatus, further comprising the power supply.

In an example embodiment of any of the above described variable conductive apparatus, further comprising a detector for detecting the detected signal.

In an example embodiment of any of the above described variable conductive apparatus, further comprising at least one layer to separate at least part of the first conductive surface and the second conductive surface.

In an example embodiment of any of the above described variable conductive apparatus, wherein the at least one layer comprises conductive threads that provide additional contact surface area for the conductive contact surface area.

In an example embodiment of any of the above described variable conductive apparatus, wherein the at least one layer further comprises non-conductive threads.

In an example embodiment of any of the above described variable conductive apparatus, wherein the at least one layer comprises an insulating layer.

In an example embodiment of any of the above described variable conductive apparatus, wherein the insulating layer comprises air.

In an example embodiment of any of the above described variable conductive apparatus, wherein the at least one layer comprises a compressible layer.

In an example embodiment of any of the above described variable conductive apparatus, further comprising a support layer to receive the applied external force and to support the first conductive path or the second conductive path, wherein the first support layer comprises at least one rigid layer.

In an example embodiment of any of the above described variable conductive apparatus, wherein the increase in conductive contact surface area comprises additional contact points between the first conductive surface and the second conductive surface.

In an example embodiment of any of the above described variable conductive apparatus, wherein the increase in conductive contact surface area comprises an increase in contact surface area of an existing conductive contact point that exists when there is no applied external force.

In an example embodiment of any of the above described variable conductive apparatus, wherein the applied external force reduces a distance between the another part of the first conductive surface and the another part of the second conductive surface.

In an example embodiment of any of the above described variable conductive apparatus, wherein the conductive contact surface area increases in correlation to the applied external force, resulting in the increase in the conductivity.

In an example embodiment of any of the above described variable conductive apparatus, wherein the first conductive path comprises a material having a first conductivity, wherein the second conductive path comprises a material having a second conductivity that is different than the first conductivity.

In an example embodiment of any of the above described variable conductive apparatus, wherein the first conductive path is generally perpendicular to the second conductive path, and the first and second conductive paths overlap in a grid-like pattern.

In an example embodiment of any of the above described variable conductive apparatus, wherein at least one of the first conductive path or the second conductive path is in a spiral pattern.

In an example embodiment of any of the above described variable conductive apparatus, wherein the applied external force increases conductive contact surface area between the another part of the first conductive surface and the another part of the second conductive surface.

In an example embodiment of any of the above described variable conductive apparatus, wherein the applied force comprises vibration.

In an example embodiment of any of the above described variable conductive apparatus, wherein the first conductive path and the second conductive path are comprised of conductive fabrics and/or threads.

An example embodiment is a sensor sheet comprising one or more layers and a plurality of sensors, each of the sensors comprising any of the above described variable conductive; a power supply for providing power to the first conductive paths; and a detector for detecting a detectable signal from the second conductive paths in dependence of the conductivity of the variable conductive apparatuses.

In an example embodiment of any of the above described sensor sheet, wherein each sensor shares the respective first conductive path with the first conductive path of at least one of the other sensors, and wherein each sensor shares the respective second conductive path with the second conductive path of different at least one of the other sensors, wherein power is selectively activatable to each of the first conductive paths one at a time, and a detectable signal from one or more of the second conductive paths results in knowledge of which of the sensors is receiving the applied external force.

In an example embodiment of any of the above described sensor sheet, wherein the sensors are arranged in an array.

In an example embodiment of any of the above described sensor sheet, wherein the first conductive paths of the sensors are arranged in columns and the second conductive paths of the sensors are arranged in rows, wherein power is selectively activatable to each of the first conductive paths one at a time, and a detectable signal from one or more of the second conductive paths results in knowledge of which of the sensors is receiving the applied external force.

In an example embodiment of any of the above described sensor sheet, wherein the at least one layer comprises at least one flexible layer.

In an example embodiment of any of the above described sensor sheet, wherein the at least one layer comprises at least one rigid layer.

Another example embodiment is a variable pressure sensor comprising any of the above described variable conductive apparatus; a power supply for providing power to the first conductive paths; and a detector for detecting a detectable signal from the second conductive paths in dependence of the conductivity of the variable conductive apparatuses.

Another example embodiment is printed circuit board or microchip comprising any of the above described variable conductive apparatus, the printed circuit board or microchip configured to perform digital communication over the variable conductive apparatus over greater than two signal states due to dynamic range of the conductivity of the variable conductive apparatus.

Another example embodiment is a system for monitoring external force comprising: a power supply; one or more variable pressure sensors, each comprising any of the above described variable conductive apparatus for receiving power from the power supply; a detector for detecting a detectable signal from the variable conductive apparatuses in dependence of the conductivity of the variable conductive apparatuses; a processor for processing the detectable signal into external force data, and for sending the external force data to a database or a server for storing and analyzing of the external force data; and an output device controlled by the processor to communicate an output in response to the detectable signal or the analyzed external force data.

In an example embodiment of any of the above described system, further comprising a microcontroller, a single board computer that includes a wireless and wired network capabilities, one or more multiplexers, one or more analog-digital converters, one or more amplifiers, an alerting device, one or more speakers, one or more buzzers, one or more LEDs, one or more LED strips, or a combination or a subcombination thereof.

In an example embodiment of any of the above described system, wherein the output device further comprises a sensory feedback system for user interaction through the output device.

In an example embodiment of any of the above described system, wherein the sensory feedback system comprises an alarm for alerting incidents.

In an example embodiment of any of the above described system, wherein the database is part of a cloud server.

In an example embodiment of any of the above described system, further comprising a timer system for initiating a notification based on a predetermined set of parameters.

In an example embodiment of any of the above described system, wherein the database further comprises a processor for analyzing the external force data.

Another example embodiment is a method of monitoring movement using any of the above described system, the method comprising: determining a baseline external force value when there is no external force applied to the variable conductive apparatus; obtaining signals having values above the baseline external force value; calculating differences between the obtained signals and the baseline external force value; and identifying one or more signals having differences greater than a difference threshold; outputting information to the output device based on said identifying when the one or more signals having differences greater than the difference threshold.

In an example embodiment of any of the above described method, wherein the baseline external force value is an average value.

In an example embodiment of any of the above described method, wherein the baseline external force value is a respective value for each variable pressure sensor.

An example embodiment is a use of any of the above described system for monitoring breathing of a subject, for monitoring heart rate of a subject, for monitoring movement of a subject, for monitoring and tracking location of a subject, or for monitoring pressure level in a compression instrument.

An example embodiment is a use of any of the above described system for monitoring pressure level in a compression instrument tourniquet.

An example embodiment is a use of any of the above described system in a shelf for monitoring inventory levels.

An example embodiment is a use of any of the above described system in artificial exterior skin for providing a sense of touch to a robotic component.

While some of the present embodiments are described in terms of methods, a person of ordinary skill in the art will understand that present embodiments are also directed to various apparatus such as processors, circuitry, and controllers including components for performing at least some of the aspects and features of the described methods, be it by way of hardware components, software or any combination of the two, or in any other manner, as applicable.

In the Figures, as applicable, at least some or all of the illustrated subsystems or blocks may include or be controlled by a processor, which executes instructions stored in a memory or non-transitory computer readable medium. Variations may be made to some example embodiments, which may include combinations and sub-combinations of any of the above. The various embodiments presented above are merely examples and are in no way meant to limit the scope of this disclosure. Variations of the innovations described herein will be apparent to persons of ordinary skill in the art having the benefit of the example embodiments, such variations being within the intended scope of the present disclosure. In particular, features from one or more of the above-described embodiments may be selected to create alternative embodiments comprised of a sub-combination of features, which may not be explicitly described above. In addition, features from one or more of the above-described embodiments may be selected and combined to create alternative embodiments comprised of a combination of features which may not be explicitly described above. Features suitable for such combinations and sub-combinations would be readily apparent to persons skilled in the art upon review of the present disclosure as a whole. The subject matter described herein intends to cover and embrace all suitable changes in technology.

Certain adaptations and modifications of the described embodiments can be made. Therefore, the above discussed embodiments are considered to be illustrative and not restrictive.

What is claimed is:

1. A variable conductive apparatus responsive to applied external force, comprising:
   a first conductive path that includes a first conductive surface;
   a second conductive path that includes a second conductive surface, a part of the second conductive surface having a conductive contact surface area with a part of the first conductive surface when there is no applied external force, another part of the second conductive surface is separate from another part of the first conductive surface when there is no applied external force, wherein the applied external force increases the conductive contact surface area between the first conductive surface and the second conductive surface resulting in an increase in conductivity between the first conductive surface and the second conductive surface; and
   at least one layer to separate at least part of the first conductive surface and the second conductive surface, the at least one layer comprises conductive threads that provide additional contact surface area for the conductive contact surface area.

2. A variable conductive apparatus as claimed in claim 1, further comprising a power supply, wherein the first conductive path is for receiving power from the power supply, and the second conductive path results in a detectable signal that varies in dependence of the conductivity.

3. A variable conductive apparatus as claimed in claim 2, wherein the power supply is a DC voltage power supply.

4. A variable conductive apparatus as claimed in claim 2, wherein the detectable signal is less than a maximum signal defined by the power supply when there is no applied external force.

5. A variable conductive apparatus as claimed in claim 4, wherein the detectable signal increases in correlation to the applied external force due to the increase in the conductivity.

6. A variable conductive apparatus as claimed in claim 2, wherein the detectable signal is a maximum signal defined by the power supply when there is applied external force that maximizes the conductive contact surface area, resulting in maximized conductivity.

7. A variable conductive apparatus as claimed in claim 2, further comprising a detector for detecting the detected signal.

8. A variable conductive apparatus as claimed in claim 1, wherein the at least one layer further comprises non-conductive threads.

9. A variable conductive apparatus as claimed in claim 1, wherein the at least one layer comprises a compressible layer.

10. A variable conductive apparatus as claimed in claim 1, further comprising a support layer to receive the applied external force and to support the first conductive path or the second conductive path, wherein the support layer comprises at least one rigid layer.

11. A variable conductive apparatus as claimed in claim 1, wherein the increase in conductive contact surface area comprises additional contact points between the first conductive surface and the second conductive surface.

12. A variable conductive apparatus as claimed in claim 1, wherein the increase in conductive contact surface area comprises an increase in contact surface area of an existing conductive contact point that exists when there is no applied external force.

13. A variable conductive apparatus as claimed in claim 1, wherein the applied external force reduces a distance between the another part of the first conductive surface and the another part of the second conductive surface.

14. A variable conductive apparatus as claimed in claim 1, wherein the conductive contact surface area increases in correlation to the applied external force, resulting in the increase in the conductivity.

15. A variable conductive apparatus as claimed in claim 1, wherein the first conductive path comprises a material having a first conductivity, wherein the second conductive path comprises a material having a second conductivity that is different than the first conductivity.

16. A variable conductive apparatus as claimed in claim 1, wherein the first conductive path is generally perpendicular to the second conductive path, and the first and second conductive paths overlap in a grid-like pattern.

17. A variable conductive apparatus as claimed in claim 1, wherein at least one of the first conductive path and the second conductive path is in a spiral pattern.

18. A variable conductive apparatus as claimed in claim 1, wherein the applied external force increases conductive contact surface area between the another part of the first conductive surface and the another part of the second conductive surface.

19. A variable conductive apparatus as claimed in claim 1, wherein the applied force comprises vibration.

20. A variable conductive apparatus as claimed in claim 1, wherein the first conductive path and the second conductive path are comprised of conductive fabric and/or threads.

21. A sensor sheet comprising one or more layers and a plurality of sensors, each of the sensors comprising a variable conductive apparatus as claimed in claim 1; a power supply for providing power to the first conductive path of each variable conductive apparatus; and a detector for detecting a detectable signal from the second conductive path of each variable conductive apparatus, wherein the detectable signal varies in dependence of the conductivity of the variable conductive apparatuses.

22. A sensor sheet as claimed in claim 21, wherein each sensor shares the respective first conductive path with the first conductive path of at least one of the other sensors, and wherein each sensor shares the respective second conductive path with the second conductive path of different at least one of the other sensors, wherein power is selectively activatable to each of the first conductive paths one at a time, and a detectable signal from one or more of the second conductive paths results in knowledge of which of the sensors is receiving the applied external force.

23. A variable pressure sensor comprising a variable conductive apparatus as claimed in claim 1; a power supply for providing power to the first conductive path; and a detector for detecting a detectable signal from the second conductive path, wherein the detectable signal varies in dependence of the conductivity of the variable conductive apparatuses.

24. A printed circuit board or microchip comprising a variable conductive apparatus as claimed in claim 1, the printed circuit board or microchip configured to perform digital communication over the variable conductive apparatus over greater than two signal states due to dynamic range of the conductivity of the variable conductive apparatus.

25. A system for monitoring external force comprising:
 a power supply;
 one or more variable pressure sensors, each comprising a variable conductive apparatus as claimed in claim 1 receiving power from the power supply;
 a detector for detecting a detectable signal from the variable conductive apparatuses in dependence of the conductivity of the variable conductive apparatuses;
 a processor for processing the detectable signal into external force data, and for sending the external force data to a database or a server for storing and analyzing of the external force data; and
 an output device controlled by the processor to communicate an output in response to the detectable signal or the analyzed external force data.

26. Use of a system as claimed in claim 25 for monitoring breathing of a subject, for monitoring heart rate of a subject, for monitoring movement of a subject, for monitoring and tracking location of a subject, or for monitoring pressure level in a compression instrument.

27. Use of a system as claimed in claim 25 for monitoring pressure level in a compression instrument tourniquet.

28. Use of a system as claimed in claim 25 in a shelf for monitoring inventory levels.

29. Use of a system as claimed in claim 25 in artificial exterior skin for providing a sense of touch to a robotic component.

30. A compression instrument tourniquet that is responsive to applied external force, comprising:
 a first conductive path that includes a first conductive surface; and
 a second conductive path that includes a second conductive surface, a part of the second conductive surface having a conductive contact surface area with a part of the first conductive surface when there is no applied external force, another part of the second conductive surface is separate from another part of the first conductive surface when there is no applied external force,
 wherein the applied external force increases the conductive contact surface area between the first conductive surface and the second conductive surface resulting in an increase in conductivity between the first conductive surface and the second conductive surface.

31. A variable conductive apparatus responsive to applied external force, comprising:
 a first conductive path that includes a first conductive surface; and
 a second conductive path that includes a second conductive surface, a part of the second conductive surface having a conductive contact surface area with a part of the first conductive surface when there is no applied external force, another part of the second conductive surface is separate from another part of the first conductive surface when there is no applied external force,
 wherein the applied external force increases the conductive contact surface area between the first conductive surface and the second conductive surface resulting in an increase in conductivity between the first conductive surface and the second conductive surface,
 wherein the increase in conductive contact surface area comprises additional contact points between the first conductive surface and the second conductive surface.

32. A printed circuit board or microchip comprising a variable conductive apparatus as claimed in claim 31, the printed circuit board or microchip configured to perform digital communication over the variable conductive apparatus over greater than two signal states due to dynamic range of the conductivity of the variable conductive apparatus.

* * * * *